US007815612B2

(12) United States Patent
Cise et al.

(10) Patent No.: US 7,815,612 B2
(45) Date of Patent: Oct. 19, 2010

(54) APPARATUS AND METHOD FOR PREVENTING FREE FLOW IN AN INFUSION LINE

(75) Inventors: David Cise, Riverton, UT (US); David J. McNally, Salt Lake City, UT (US); Kent F. Beck, Salt Lake City, UT (US); Blake Allen, Murray, UT (US); John Dickey, Bountiful, UT (US)

(73) Assignee: Zevex, Inc., Salt Lake City, UT (US)

( * ) Notice: Subject to any disclaimer, the term of this patent is extended or adjusted under 35 U.S.C. 154(b) by 1059 days.

(21) Appl. No.: 11/226,856

(22) Filed: Sep. 14, 2005

(65) Prior Publication Data
US 2006/0058740 A1   Mar. 16, 2006

Related U.S. Application Data

(63) Continuation-in-part of application No. 10/317,027, filed on Dec. 11, 2002, now Pat. No. 7,150,727, which is a continuation-in-part of application No. 09/836,850, filed on Apr. 16, 2001, now Pat. No. 6,979,311, which is a continuation-in-part of application No. 09/569,332, filed on May 11, 2000, now Pat. No. 6,595,950.

(51) Int. Cl.
*A61M 5/00* (2006.01)
*A61M 5/14* (2006.01)
(52) U.S. Cl. .................. 604/246; 604/247; 604/256
(58) Field of Classification Search ............. 604/246, 604/247, 256; 417/476–477.14
See application file for complete search history.

(56) References Cited

U.S. PATENT DOCUMENTS 584,091 A    6/1897  Leidich

| 2,471,623 A | 5/1949 | Hubbell |
| 2,518,165 A | 8/1950 | Millard |
| 2,858,095 A | 10/1958 | Harris et al. |
| 2,999,499 A | 9/1961 | Willet |
| 3,213,882 A | 10/1965 | Beatty |

(Continued)

FOREIGN PATENT DOCUMENTS

DE    2920366    11/1980

(Continued)

OTHER PUBLICATIONS

Office action from related U.S. Appl. No. 11/135,608, Mail Date: Feb. 22, 2007.

*Primary Examiner*—Kevin C Sirmons
*Assistant Examiner*—Andrew M Gilbert
(74) *Attorney, Agent, or Firm*—Bateman IP Law Group

(57) ABSTRACT

An apparatus and method for preventing free flow through an infusion set utilizes an occluder disposed within the infusion set to selectively prevent flow therethrough. The occluder may be responsive to a pressure differential within the infusion set or may respond to compression of the infusion set. The occluder may also be configured to allow flow when the infusion set adjacent the occluder is moved sideways relative to the occluder or maintained at an angle relative to the occluder. When a pair of occluders are used in sequence, an in-line pump may be formed.

44 Claims, 30 Drawing Sheets

U.S. PATENT DOCUMENTS

| | | |
|---|---|---|
| 3,329,391 A | 7/1967 | Deane |
| 3,707,972 A | 1/1973 | Villari et al. |
| 3,985,140 A | 10/1976 | Harris |
| 3,998,364 A | 12/1976 | Hollander |
| 4,037,596 A | 7/1977 | LeFevre et al. |
| 4,063,555 A | 12/1977 | Ulinder |
| 4,065,093 A | 12/1977 | Phillips |
| 4,106,675 A | 8/1978 | Taylor |
| 4,142,645 A | 3/1979 | Walton |
| 4,160,383 A | 7/1979 | Rauschenberger |
| 4,230,151 A | 10/1980 | Jonsson |
| 4,236,880 A | 12/1980 | Archibald |
| 4,300,571 A | 11/1981 | Waldbillig |
| 4,381,591 A | 5/1983 | Barger et al. |
| 4,382,453 A | 5/1983 | Bujan et al. |
| 4,425,116 A | 1/1984 | Bilstad et al. |
| 4,430,073 A | 2/1984 | Bemis et al. |
| 4,453,295 A | 6/1984 | Laszczower |
| 4,465,489 A | 8/1984 | Jenkins et al. |
| 4,498,843 A | 2/1985 | Schneider et al. |
| 4,524,802 A | 6/1985 | Lawrence et al. |
| 4,527,588 A * | 7/1985 | Tseo et al. ............. 137/565.11 |
| 4,559,045 A | 12/1985 | Danby et al. |
| 4,560,375 A | 12/1985 | Schulte et al. |
| 4,579,553 A | 4/1986 | Urquhart et al. |
| 4,596,557 A | 6/1986 | Pexa |
| 4,624,663 A | 11/1986 | Danby et al. |
| 4,634,092 A | 1/1987 | Daniell et al. |
| 4,645,489 A | 2/1987 | Krumme et al. |
| 4,689,043 A | 8/1987 | Bisha |
| 4,728,324 A | 3/1988 | Steigerwald et al. |
| 4,730,635 A | 3/1988 | Linden |
| 4,913,401 A | 4/1990 | Handke |
| 4,932,938 A | 6/1990 | Goldberg et al. |
| 4,935,010 A | 6/1990 | Cox et al. |
| 4,960,259 A | 10/1990 | Sunnanvader et al. |
| 5,020,562 A | 6/1991 | Richmond et al. |
| 5,022,422 A | 6/1991 | Di Palma |
| 5,083,561 A | 1/1992 | Russo |
| 5,098,406 A | 3/1992 | Sawyer |
| 5,151,019 A | 9/1992 | Danby et al. |
| 5,219,327 A | 6/1993 | Okada |
| 5,232,193 A | 8/1993 | Skakoon |
| 5,238,218 A | 8/1993 | Mackal |
| 5,257,978 A | 11/1993 | Haber et al. |
| 5,261,459 A | 11/1993 | Atkinson et al. |
| 5,265,847 A | 11/1993 | Vorhis |
| 5,336,174 A | 8/1994 | Daoud et al. |
| 5,395,351 A | 3/1995 | Munsch |
| 5,396,925 A | 3/1995 | Poli |
| 5,474,544 A | 12/1995 | Lynn |
| 5,514,102 A | 5/1996 | Winterer et al. |
| 5,522,799 A | 6/1996 | Furukawa |
| 5,531,713 A | 7/1996 | Mastronardi et al. |
| 5,556,386 A | 9/1996 | Todd |
| 5,578,070 A | 11/1996 | Utterberg |
| 5,704,584 A * | 1/1998 | Winterer et al. ................. 251/7 |
| 5,720,721 A | 2/1998 | Dumas et al. |
| 5,772,255 A * | 6/1998 | Osborne et al. ............... 285/38 |
| 5,807,312 A | 9/1998 | Dzwonkiewicz |
| 5,810,323 A * | 9/1998 | Winterer et al. ................. 251/4 |
| 5,826,621 A | 10/1998 | Jemmott |
| 5,853,397 A | 12/1998 | Shemesh et al. |
| 5,971,357 A | 10/1999 | Denton et al. |
| 6,017,332 A | 1/2000 | Urrutia |
| 6,092,695 A | 7/2000 | Loeffler |
| 6,142,979 A | 11/2000 | McNally et al. |
| 6,183,447 B1 | 2/2001 | Urrutia |
| 6,196,992 B1 | 3/2001 | Keilman et al. |
| 6,209,538 B1 | 4/2001 | Casper et al. |
| D455,489 S | 4/2002 | Beck et al. |
| 6,398,758 B1 | 6/2002 | Jacobson et al. |
| 6,398,780 B1 | 6/2002 | Farley et al. |
| 6,454,742 B1 * | 9/2002 | Noecker et al. ............. 604/131 |
| 6,461,335 B1 * | 10/2002 | Noecker .................... 604/246 |
| 6,494,864 B1 * | 12/2002 | Kerwin et al. .............. 604/131 |
| 6,523,414 B1 * | 2/2003 | Malmstrom et al. .......... 73/705 |
| 6,531,708 B1 | 3/2003 | Malmstrom et al. |
| 6,585,499 B2 | 7/2003 | Nguyen et al. |
| 6,595,950 B1 * | 7/2003 | Miles et al. ................... 604/80 |
| 6,623,447 B2 | 9/2003 | Miles et al. |
| 6,659,976 B2 * | 12/2003 | Beck et al. .................... 604/67 |
| 6,666,665 B1 | 12/2003 | Nguyen et al. |
| 6,685,670 B2 | 2/2004 | Miles et al. |
| 6,750,468 B2 | 6/2004 | Malmstrom et al. |
| 6,852,094 B2 | 2/2005 | Beck et al. |
| D503,978 S | 4/2005 | Beck |
| 6,907,788 B2 | 6/2005 | Malmstrom et al. |
| 6,923,785 B2 | 8/2005 | Miles et al. |
| 6,979,311 B2 * | 12/2005 | Miles et al. ................... 604/80 |
| 7,070,575 B2 * | 7/2006 | Beck et al. .................... 604/67 |
| 7,150,727 B2 * | 12/2006 | Cise et al. .................... 604/246 |
| 7,367,963 B2 * | 5/2008 | Cise et al. .................... 604/246 |
| 2002/0127708 A1 | 9/2002 | Kluttz et al. |
| 2002/0151838 A1 | 10/2002 | Beck et al. |
| 2003/0125674 A1 * | 7/2003 | Cise et al. .................... 604/247 |
| 2004/0220542 A1 | 11/2004 | Cise et al. |
| 2005/0119625 A1 | 6/2005 | Miles et al. |
| 2005/0178206 A1 | 8/2005 | Malmstrom et al. |
| 2005/0209552 A1 | 9/2005 | Beck et al. |
| 2006/0058740 A1 | 3/2006 | Cise et al. |

FOREIGN PATENT DOCUMENTS

| | | |
|---|---|---|
| DE | 2939794 | 4/1981 |
| DE | 29604737 | 7/1997 |
| EP | 0 150 666 | 8/1985 |
| EP | 0 276 356 | 8/1988 |
| EP | 0276356 | 8/1988 |
| EP | 0 423 978 | 4/1991 |
| EP | 0 483 794 | 5/1992 |
| GB | 2225065 | 5/1990 |
| WO | WO 96-17636 | 6/1996 |
| WO | WO 96/17636 | 6/1996 |
| WO | WO 98/05378 | 2/1998 |

* cited by examiner

APPARATUS AND METHOD FOR PREVENTING FREE FLOW IN AN INFUSION LINE

RELATED APPLICATIONS

The present application is a continuation-in-part of U.S. patent application Ser. No. 10/317,027, filed Dec. 11, 2002, U.S. Pat. No. 7,150,727, which is a continuation-in-part of U.S. patent application Ser. No. 09/836,850, filed Apr. 16, 2001, U.S. Pat. No. 6,979,311, which is a continuation-in-part of U.S. patent application Ser. No. 09/569,332, filed May 11, 2000, U.S. Pat. No. 6,595,950.

BACKGROUND OF THE INVENTION

1. Field of the Invention

The present invention relates to an apparatus and method for preventing free flow during enteral or parenteral administration of solutions through an infusion line. More particularly, the present invention relates to an occluder/valve and method of use for infusion sets and the like, wherein the occluder/valve prevents undesirable free-flow of solution through the infusion set while allowing controlled flow through the infusion set.

2. State of the Art

The use of infusion sets to administer solutions to patients is well known in the medical arts. Infusion sets are used for both enteral and parenteral applications. Enteral feeding pumps are used to provide patients with nutrition and medication when they are unable, for a variety of reasons, to eat normally. Various solutions are provided to patients to ensure adequate hydration and to provide needed nutrients, minerals and medication. Often, the infusion set is placed in a free standing arrangement in which gravity forces the solution into the patient. The rate at which the solution enters the patient can be roughly controlled by various clamps, such as roller clamps, which are currently available on the market.

In many applications, it is necessary to precisely control the amount of solution which enters the patient. When this is the case, a regulating device, such as an enteral feeding pump, is placed along the infusion set to control the rate at which the solution is fed to the patient. In applications where a pump, etc., is used, the clamps used to regulate flow are typically opened to their fullest extent to prevent the clamp from interfering with the proper functioning of the pump. The clamp is opened with the expectation that the enteral feeding pump will control fluid flow through the infusion set.

It is not uncommon, however, for emergencies or other distractions to prevent the medical personnel from properly loading the infusion set in the enteral feeding pump. A problem of anticipated flow may occur where an undesired amount of a solution is delivered to a patient. Unanticipated flow may involve unchecked flow, as may be known as free flow, or may simply involve greater than desired flow. Unanticipated flow may occur where there is an improperly loaded infusion set, etc. Thus, the present invention is directed towards preventing unanticipated flow through the infusion set, and is hereafter referred to as preventing "free-flow" for simplicity throughout the application. When the infusion set is not properly loaded in the pump and the clamp has been opened, a situation known as free-flow often develops. The force of gravity causes the solution to flow freely into the patient unchecked by the pump or other regulating device. Under a free-flow condition, an amount of solution many times the desired dose can be supplied to the patient within a relatively short time period. This can be particularly dangerous if the solution contains potent medicines and/or the patient's body is not physically strong enough to adjust to the large inflow of solution.

Numerous devices have been developed in an attempt to prevent free flow conditions. Such devices, however, typically add significantly to the overall cost of the infusion set and some provide only marginal protection against free flow.

Thus, there is a need for a device that prevents a free-flow condition while allowing controlled flow through the infusion set. There is also a need for such a device which prevents free-flow if an infusion set is not properly mounted in a pump or other regulating means. Furthermore, there is a need for a device which prevents free-flow and which is inexpensive and easy to use.

SUMMARY OF THE INVENTION

It is an object of the present invention to provide an apparatus and method for occluding infusion sets to prevent an accidental free-flow condition.

It is another object of the present invention to provide an occluder which is simple to make and use.

It is another object of the present invention to provide such an occluder which is relatively inexpensive.

It is still another object of the present invention to provide an occluder which occludes fluid flow through the infusion set unless the infusion set is properly loaded in a flow control mechanism such as an enteral feeding pump.

It is still yet another aspect of the present invention to provide an occluder which functions as at least part of a valve to effectively control fluid flow through a conduit.

One or more of the above and other objects of the invention are realized in an apparatus and method for preventing free flow in an infusion set. In accordance with one aspect of the invention, an occluder is disposed within the infusion set. The occluder is configured to prevent free flow of fluids in the infusion set past the occluder. The occluder is also configured, however, to selectively allow solutions to pass by the occluder which are pumped by an enteral feeding pump and the like. It will be appreciated that all embodiments shown or claimed need not accomplish each objective.

In accordance with one embodiment of the invention, the occluder is formed by a stop placed in the tubing of the infusion set. The stop limits flow through the tube by limiting flow around and/or through the stop when the solution is subject to flow due to gravity. However, when greater pressures are placed on the solution, such as those produced by a pump, the solution is able to flow around and/or through the stop, thereby delivering the solution to the patient.

In accordance with another embodiment of the present invention, an occluding valve is disposed in the infusion set. The valve prevents free flow through the infusion set due to gravity, while allowing controlled flow of solution through the infusion set.

In accordance with another aspect of the invention, the occluder is configured to stop fluid flow until the infusion set has been properly loaded into a control mechanism such as a pump. Once properly placed, the interaction between the occluder, the infusion set, and the pump effectively engages the infusion set to allow solution to flow therethrough.

In accordance with still another aspect of the present invention, the occluder can be formed integrally with the infusion set or can be formed of independent piece(s) which are then placed in the infusion set to selectively occlude the flow of solution therethrough.

In accordance with still yet another aspect of the invention, the occluder can function as a valve to selectively allow fluid flow therethrough. In one embodiment, a pair of occluders and infusion line can be used in conjunction with a piston or other force applicator to form a pump which delivers predetermined amounts of fluid to a patient.

In accordance with still yet another aspect of the present invention, the occluder and infusion line can be formed to nest in and be opened by a conventional fluid flow pump.

In accordance with another aspect of the present invention, the occluder and infusion set may be disposed in the pump such that the tubing of the infusion set is held at an angle relative to the axis of the occluder. The tubing may be held at such an angle to modify the sealing characteristics of the occluder. In one embodiment, the pump is formed such that when the infusion set is loaded by wrapping the tubing around the pump rotor, the infusion set tubing is held at an angle relative to the occluder such that an opening is formed between the occluder and the infusion set. In another embodiment, the pump is designed such that an arm or protrusion associated with the pump is moved into a position whereby the arm pushes on the infusion set tubing near the occluder sufficient to form an opening between the occluder and the tubing.

BRIEF DESCRIPTION OF THE DRAWINGS

The above and other objects, features, and advantages of the invention will become apparent from a consideration of the following detailed description presented in connection with the accompanying drawings in which:

FIG. 21 shows a fragmented cross-sectional view of an infusion set tubing and occluder according to the present invention being acted on by a projection from an enteral feeding pump or the like;

DETAILED DESCRIPTION

Reference will now be made to the drawings in which the various elements of the present invention will be given numeral designations and in which the invention will be discussed so as to enable one skilled in the art to make and use the invention. It is to be understood that the following description is only exemplary of the principles of the present invention, and should not be viewed as narrowing the pending claims. Additionally, while various embodiments will achieve some of the objectives set forth above, it will be understood that some embodiments may not achieve all of the objectives and the objectives should not be viewed as limiting the pending claims.

Figure 1:
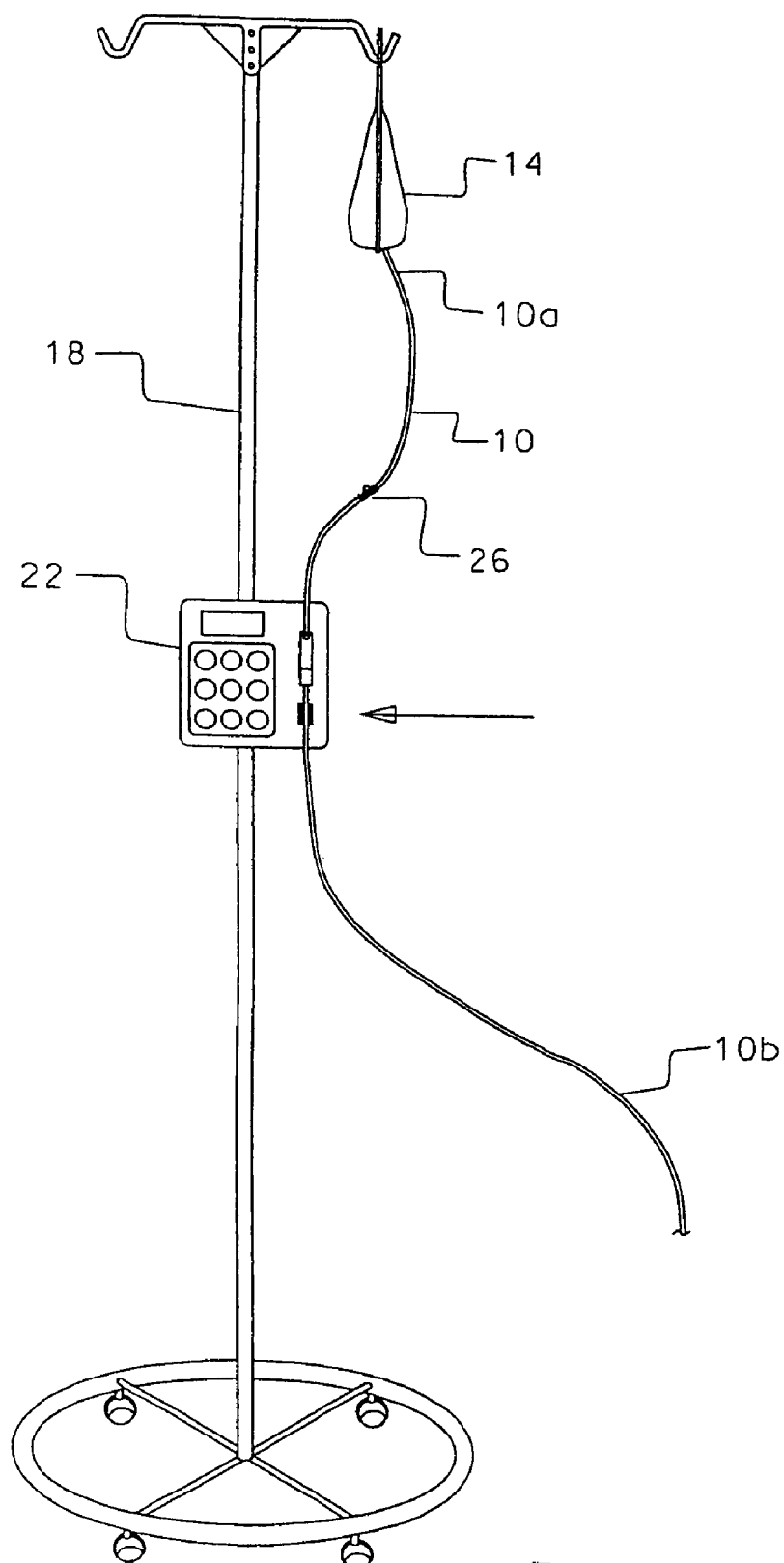
FIG. 1 shows a perspective view of an infusion set made in accordance with the prior art.

Referring to FIG. 1, there is shown a perspective view of an infusion set 10 and related structures in accordance with the teachings of the prior art. Disposed at one end 10a of the infusion set 10 is a bag 14 for holding parenteral or enteral solutions. Typically, the bag 14 is supported by a stand 18 which holds the bag approximately 6 feet off the floor.

The opposing end 10b of the infusion set 10 is connected to a patient (not shown). In a parenteral use, the end of the infusion set 10 would have a needle or intravenous catheter attached thereto which extends into the patient's venous system. In a enteral use, the end 10b would typically have a fitting which attached to a balloon catheter (not shown) mounted in a stoma in the patient's stomach. The end may also be connected to a nasoenteric feeding tube.

Solution flows under gravity from the upper end 10a of the infusion set 10 to the lower end 10b. The pressure on the fluid is approximately 0.433 psi per foot. Thus, if the bag 14 is disposed five feet higher than the patient, the pressure at the lower end 10b of the infusion set 10 is about 2.165 psi. From the extreme height of 8 feet to the floor, the solution in the infusion set 10 can reach approximately 3.5 psi.

To control the flow of solution through the infusion set 10, the infusion set is typically mounted through a flow control portion of a pump 22. The pump 22 selectively allows a metered amount of solution to pass distally (downstream) from the pump. This can be accomplished in multiple ways. For example, many enteral feeding pumps are rotary peristaltic pumps which have a rotor which engages the infusion set 10 with a plurality of rollers. Each partial rotation of the rotor allows a predetermined dose to pass to the patient. By controlling the rate at which the rotor turns, the pump can provide highly accurate doses of the solution.

Other pumps known in the art, such as linear peristaltic pumps, control solution flow through the infusion set 10 by a plurality of fingers which engage the infusion set. By controlling the position and frequency of the engagement of the fingers against the infusion set 10, a highly accurate dose can be provided to the patient.

While the pump 22 controls the solution flow through the infusion set 10 when the infusion set is properly loaded, failure to load the infusion set properly in the pump can quickly result in a free flow condition in which the solution flows uncontrolled through the infusion set. To prevent free flow, a clamp 26 is disposed along the infusion set 10. Typically, the clamp 26 is disposed above the pump 22. One common type of clamp 26 is a roller clamp which allows some control over the presence of flow and flow volume through the infusion set 10. Other clamps simply provide on/off control.

While the infusion set 22 should be mounted in the pump 22 prior to or immediately after opening the clamp, this is not always done. There are many situations in a hospital or nursing home setting in which the nurse or physician is called away or otherwise distracted prior to proper placement of the infusion set 10. If the clamp has already been opened, the result is that the solution in the bag 18 flows uncontrolled into the patient.

Thus, problems may occur where an infusion set is not properly mounted into the infusion pump. Additionally, problems such as free flow may occur where an individual forgets to load the infusion set into the pump. A third situation where problems may occur is where an infusion set may be accidentally removed from an infusion pump, such as where the infusion set may catch on another piece of equipment or on another person and be pulled from the pump.

In many situations, the free flow of the solution will cause no real threat to the patient. In some situations, however, free flow can cause serious injury or even death to the patient. For example, a critically ill patient may suffer severe shock if a large amount of solution were to suddenly flow into his or her body. Likewise, a patient receiving heavily medicated solution may be seriously injured if a solution that was designed to be delivered over a number of hours were delivered in a few minutes.

To resolve such concerns, pinch clips may be disposed on the infusion set 10. The pinch clip automatically closes the infusion set unless it is properly mounted in the infusion set 10. An example of such a pinch clip is disclosed in U.S. Pat. No. 5,810,323.

While pinch clip occluders are a significant advantage over the possibility of free flow, they are relatively expensive to make. While such an occluder may only cost ten to twenty cents, using a new occluder with every infusion set adds a proportionally significant amount to the cost of an infusion set. Thus, there is a need to find an apparatus and method for preventing free flow in an infusion set which is reliable and which is less expensive than the prior art.

Figure 2A:
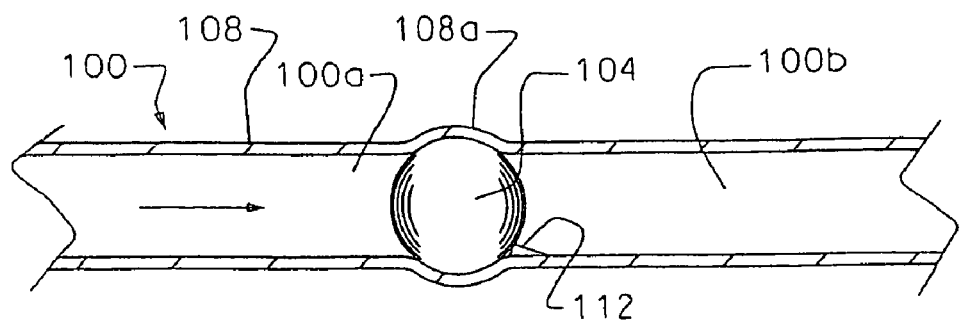
FIG. 2A shows a fragmented, side cross-sectional view of an apparatus and method for preventing free-flow through an infusion set in the form of an occluder mounted in an infusion set with the occluder and infusion set in a closed configuration.

Turning now to FIG. 2A, there is shown a fragmented, cross-sectional view of an infusion set, generally indicated at 100, with a stop or occluder 104 disposed therein. The infusion set 100 is formed by one or more elongate tubes 108 made of a flexible, resilient material such as silicone rubber, latex, polyurethane, neoprene or numerous similar medical grade materials. (In light of the present disclosure, those skilled in the art will appreciate that the present invention may be used in nonmedical contexts as well. In such situations, the tube may be made of materials which are not medical grade.)

The occluder 104 has an exterior diameter which is slightly larger than the interior diameter of the tube forming the infusion set 100. This causes a portion 108a of the tube to stretch slightly as it passes over the occluder 104.

The occluder 104 prevents flow through the infusion set 100 based on gravity. Thus, the size of the occluder 104 will depend on the material used to form the infusion set. In a presently preferred embodiment, the infusion set 100 is formed from a tube made of silicone rubber. The tube has a wall thickness of approximately 0.038 inches and an inner diameter of approximately 0.130 inches. The occluder 104 is preferably formed out of a plastic (e.g. acrylonitrile butyl styrene (ABS), acrylic (PMMA), polycarbonate, etc.) or a stainless steel ball bearing having an outer diameter of 0.141 inches.

Because the occluder 104 is larger than the interior diameter of the infusion set 100, solution which is under only the force of gravity will back-up behind the occluder and not pass. To prevent the occluder 104 from gradually working its way downstream, a projection 112 can be formed in the infusion set 100 or, as explained in detail below, the occluder may be fastened to a connector or some other stationary structure.

Figure 2B:
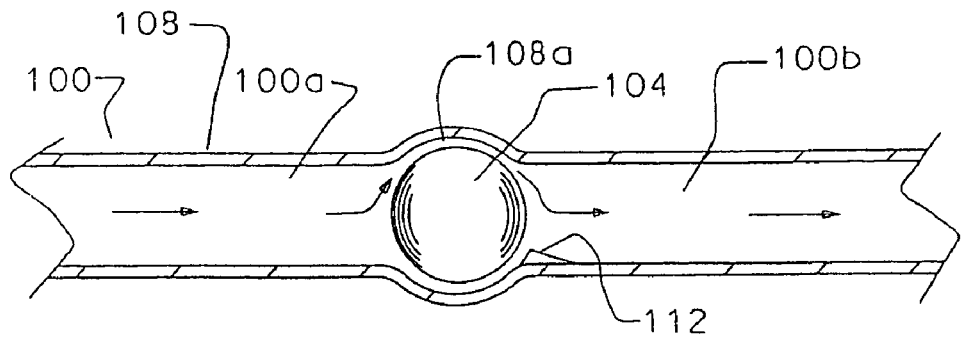
FIG. 2B shows a fragmented, side cross-sectional view similar to that of FIG. 2A, wherein the occluder and infusion set are in an open configuration.

Because this portion of the infusion set 100 is formed by an elongate, resilient tube 108, increases in pressure will cause the interior diameter of the tube to expand. When the tube 108 expands sufficiently, the portion 108a of the tube which passes over the occluder 104 allows the solution to flow around the occluder and into the distal part 100b of the infusion set 100 as shown in FIG. 2B.

Preferably, the occluder 104 and infusion set 100 are selected so that up to 4 psi can be maintained upstream of the occluder, i.e. in the proximal portion of the infusion set, before the portion 108a of the elongate tube 108 extending over the occluder will expand sufficiently to allow any clinically significant amount of solution to pass.

While solution hanging in the bag 18 may develop 2 to 3 psi due to gravity, it will not have enough pressure to pass by the occluder 104 without application of some external force. In contrast, an enteral feeding pump or other type of pump will typically generate between 5 and 15 psi. When the solution is pressurized to 5 to 15 psi by the pump, the solution is under sufficient pressure to go around the occluder 104 for delivery to the patient. In other words, if the infusion set 100 is not properly mounted in the pump so that the pump will generate a higher pressure in the proximal part 100a of the infusion set, the occluder 104 inhibits flow to the patient. Thus, there can be no free flow while accommodating flow of solution to the patient when the infusion set 100 is properly mounted in the pump.

Figure 2C:
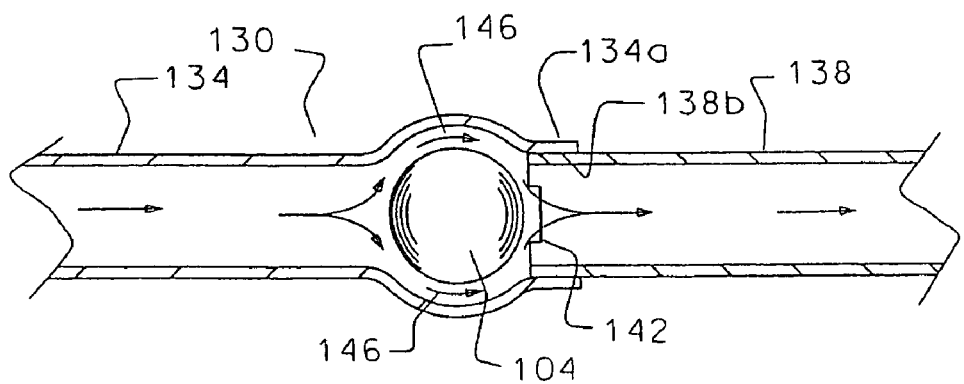
FIG. 2C shows a fragmented, side cross-sectional view of an alternate occluder/infusion set configuration made in accordance with the principles of the present invention.

Turning now to FIG. 2C, there is shown a fragmented, side cross-sectional view of an alternate configuration of an infusion set, generally indicated at 130, and the occluder 104. As with the previous embodiment, the occluder 130 is formed by a small sphere, typically formed of a biologically inert plastic or stainless steel. The infusion set 130 is formed of a first tube 134 and a second tube 138. The first tube 134 is formed of a resilient polymer or silicone so that the tube may expand with pressure. The second tube 138 is typically slightly smaller than the first tube 134 so that the distal end 134a of the first tube can be attached to the exterior of the proximal end 138a of the second tube.

To ensure that the occluder 104 does not advance distally into the second tube 138, the second tube 138 is preferably formed from a material which is semi-resilient or nonresilient and therefore will not accommodate advancement of the occluder 104. To prevent the proximal end 138a of the second tube 138 from forming a seal with the occluder 104, the proximal end preferably has one or more indentations 142 or contours formed therein. The indentations 142 or contours ensure that liquid will be able to flow around the occluder 104 even if the occluder is pressed firmly against the proximal end 138a of the second tube 138.

When pressures less than about 4 psi are disposed proximally from the occluder 104, the first tube 134 engages the occluder and prevents liquid from flowing down stream. Once the pressure on the proximal side of the occluder 104 exceeds approximately 4 psi, the distal end 134a of the first tube 134 expands and allows liquid to flow by in the manner demonstrated by arrows 146. Once the pressure subsides, the first tube 134 returns to its original size and liquid flow terminates until the pressure again is raised above the threshold.

In use, the infusion set 130 and occluder 104 prevent free flow unless the infusion set is placed in engagement with a pump that can generate sufficient pressure (psi) to compel flow around the occluder. Once past the occluder 104, the pressure of the liquid falls to a conventional level and there is no danger to the patient.

Figure 3E:
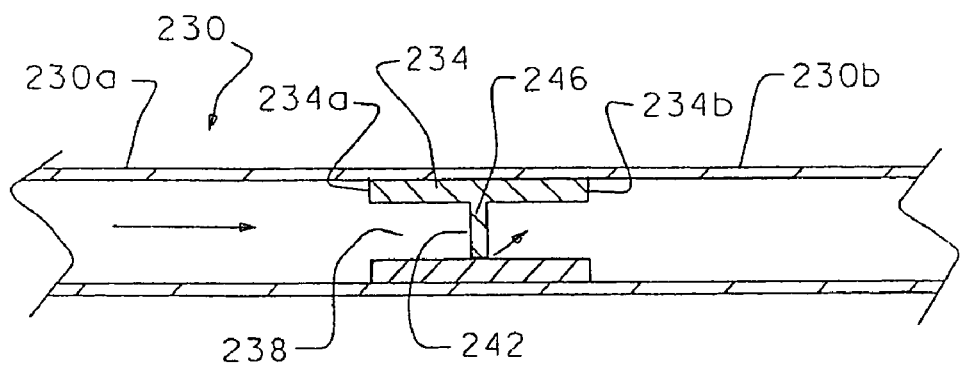
FIG. 3E shows a fragmented, side cross-sectional view of still yet another embodiment of an occluder and infusion set made in accordance with the principles of the present invention.
Figure 3A:
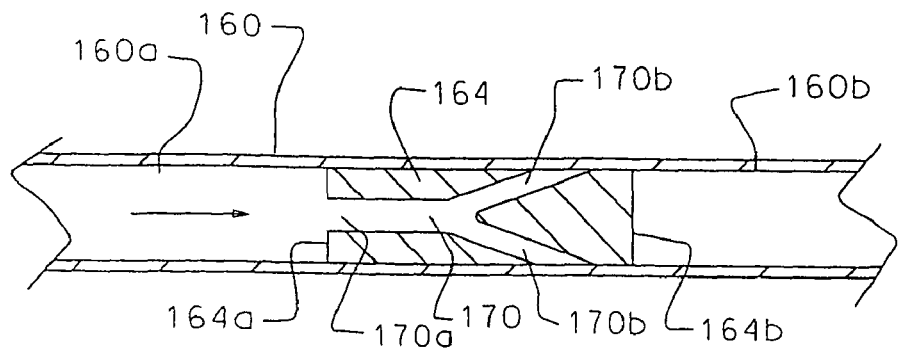
FIG. 3A shows a fragmented, side cross-sectional view of an alternate apparatus and method for preventing free-flow through an infusion set in accordance with the principles of the present invention.

Turning now to FIG. 3A, there is shown a fragmented, cross-sectional view of another embodiment of the present invention. An infusion set 160 has a proximal portion 160a and a distal portion 160b. Disposed between the proximal portion 160a and the distal portion 160b is an occluder or stop 164. The stop 164 is disposed in the infusion set 160 to selectively prevent flow from the proximal portion 160a to the distal portion 160b.

The stop 164 includes a proximal end 164a and a distal end 164b. Beginning at the proximal end 164 is a channel 170. As shown in FIG. 3A, the channel has a proximal portion 170a and two distal portions 170b which are in fluid communication with the proximal portion. While the proximal portion 170a is disposed in continuous communication with the interior of the proximal portion 160a, each of the distal portions 170b of the stop 164 are typically disposed in communication with the sidewall of the infusion set 160. The sidewall of the infusion set 160 normally prevents fluid flow out of the distal portions 170b of the channel 170.

Preferably, the sidewall will have sufficient resistance to expansion that a pressure of about 4 psi can be placed in the channel 170 without causing the infusion set 160 to radially distend or expand. Thus, if the pressure in the proximal portion 160a of the infusion set 160 is below about 4 psi, the liquid will not flow through the stop 164.

As shown in FIG. 3A, the stop 164 is relatively long. To maintain itself in place, the stop 164 frictionally engages the sidewall defining the infusion set 160. By providing a stop 164 which is long, greater surface area is provided to engage the sidewall and prevent the stop 164 from being slowly moved downstream.

Figure 3B:
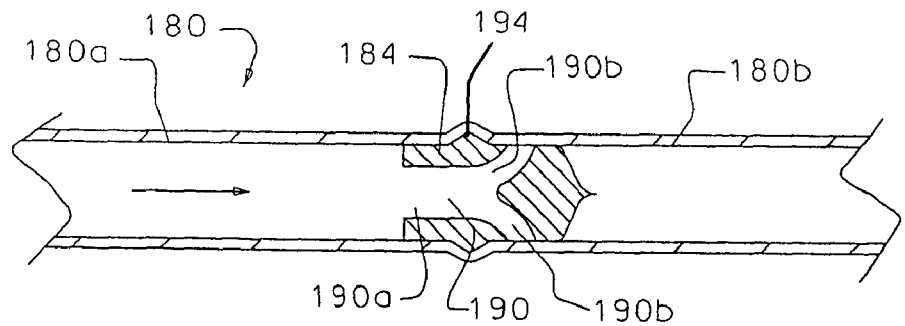
FIG. 3B shows a fragmented, cross-sectional view of an alternate occluder embodiment, with the occluder and infusion set being disposed in a closed configuration.

Turning now to FIG. 3B, there is shown a fragmented, side cross-sectional view of an infusion set, generally indicated at 180. The infusion set 180 includes a proximal (upstream) end 180a and a distal (downstream) end 180b which are separated by an occluder or stop 184. The stop 184 is similar to the stop 164 shown in FIG. 3A in that it has a channel 190 with a proximal portion 190a and a pair of distal portions 190b.

Rather than relying on an elongate body and frictional engagement with the sidewall of the infusion set 180, the stop 184 has at least one projection 194 which extends outwardly from the stop to engage the sidewall of the infusion set and prevent advancement. Preferably, the projection 194 is formed by an annular projection, or a plurality of spaced projections extending radially outwardly from the stop 184.

Figure 3C:
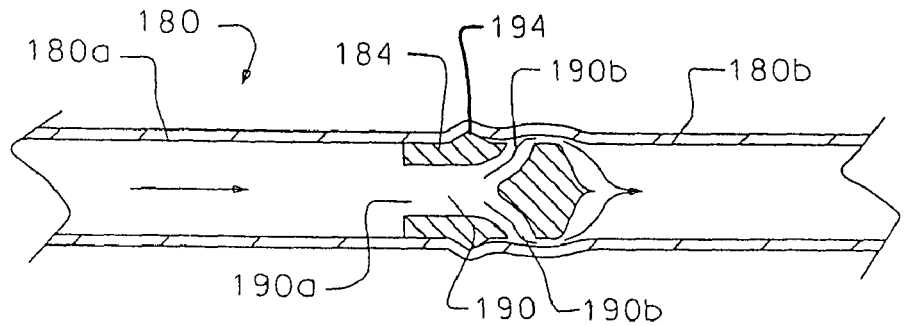
FIG. 3C shows a cross-sectional view of the occluder embodiment of FIG. 3B with the occluder and infusion set being disposed in an open configuration.

Turning now to FIG. 3C, there is shown a cross-sectional view of the infusion set 180 and stop 184 of FIG. 3B. As the pressure in the proximal portion 180a of the infusion set 180 increases to greater than about 4 psi, the infusion set will distend radially. This allows liquid contained in the proximal portion 180a of the infusion set 180 to flow into the proximal portion 190a of the channel 190, out the distal portions 190b of the channel and into the distal portion 180b of the infusion set. Once the pressure drops below about 4 psi, the infusion set 180 will radially retract and the flow in the channel 190 will be terminated as the sidewall of the infusion set covers the distal portions 190b of the channel 190.

In such a manner, the embodiments shown in FIGS. 3A through 3C prevent free flow by preventing liquid flow under 4 psi. Once the infusion set 180 is properly mounted in the pump, the increased pressure created by rotation of the rotor (or other pressure source) overcomes the restriction to flow imposed by the stop 184. When combined with the control provided by the various types of infusion pumps, the occluder or stop 164 or 184 enables a predetermined amount of liquid to flow through infusion set 160 or 180 while preventing the dangers of free flow conditions.

Figure 3D:
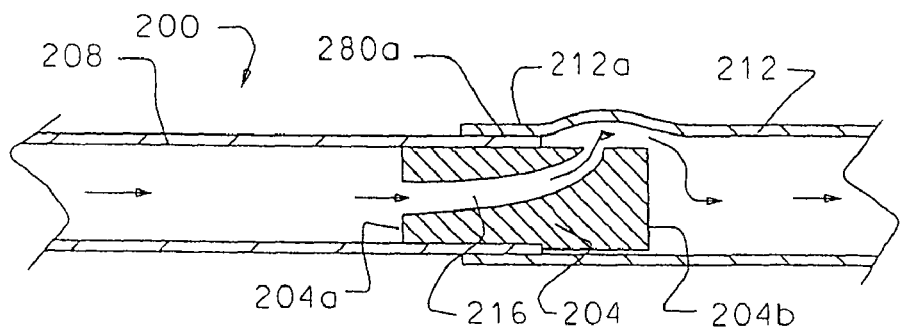
FIG. 3D shows a fragmented, side cross-sectional view of another embodiment of an occluder and infusion set made in accordance with the principles of the present invention.

FIG. 3D shows a side cross-sectional view of yet another embodiment of an infusion set, generally indicated at 200, having an occluder or stop 204 disposed therein. The infusion set 200 includes a proximal portion formed by a first tube 208 and a distal portion formed by a second tube 212. The proximal end 212a of the second tube 212 is mounted about the exterior of the distal end 208a of the first tube 208.

Disposed at the distal end 208a of the first tube 208 and the proximal end 212a of the second tube 212 is the stop 204. The stop 204 has a channel 216 extending from a proximal end 204 of the stop to a radially lateral position adjacent the distal end 204b of the stop. Thus, the channel is in fluid communication with liquid in the first tube 208, but is normally isolated from the interior of the second tube 212.

When pressures in the first tube exceed about 4 psi, the proximal end 212a of the second tube 212 radially expands, thereby opening the distal end of the channel 216 and allowing liquid to flow into the distal portion of the infusion set formed by the second tube 212.

By positioning the stop 204 at the ends of two tube segments, the stop can be adhesively attached to either of the tubes to prevent distal movement of the stop. This can be accomplished without interfering with the ability of the stop to prevent flow below about 4 psi, while allowing pressures above about 4 psi to cause liquid to pass through the infusion set.

While the embodiments of FIGS. 3A through 3D show embodiments in which the proximal end of the channel is in continuous communication with the upstream flow and the distal end of the channel is normally closed, the stop 164, 184 or 204 could be rotated so that the proximal or upstream portion of the channel is normally closed by the sidewall of the infusion set 160, 180 or 200 and the distal portion of the channel is always in communication with the distal portion of the infusion set.

FIG. 3E shows yet another embodiment of an infusion set, generally indicated at 230, and an occluder 234. The occluder 234 is disposed in the infusion set 230 so as to divide the infusion set 230 into a proximal, upstream portion 230a and a distal, downstream portion 230b.

The occluder 234 has a channel 238 which extends from a proximal end 234a of the occluder to the distal end 238b so as to form a passageway through which an infusion liquid, such as enteral feeding solution, may pass. A wall 242 is disposed along the channel 238 to selectively prevent flow through the channel. In accordance with the principles of the present invention, the wall 242 is pivotably attached to the occluder 234 in such a manner that the wall will not move to allow liquid flow through the channel until the proximal, upstream pressure exceeds 4 psi. (While described as requiring a threshold upstream pressure, in light of the present disclosure those skilled in the art will appreciate that the wall will move based on a pressure differential between the proximal and distal portions of the infusion set. Thus, the same effect could be generated by developing a vacuum downstream from the occluder 234). Those skilled in the art will appreciate that the above embodiments could be designed for other thresholds as well.

Once the desired pressure threshold has been reached, the wall 242 will pivot and open the channel 238 to flow. Once the pressure drops, the wall 242 will pivot closed in accordance with one method of use. In accordance with another method of use, however, the wall 242 can have a score 246 formed therein. The wall 242 is designed to remain occluding the infusion set 230 until the pressure threshold is exceeded. Once deflected out of the way, the wall may not return to its original position even after the pressure drop. Because the pressure increase necessary to move the wall 242 is generated by the pump (not shown), the infusion set 230 must have been properly loaded in the pump for the wall to open. When the infusion set 230 is properly loaded in the pump, the pump will prevent free flow. Thus, if the infusion set 230 is properly loaded in the pump, the occluder does not need to continue to prevent free flow.

Figure 4A:
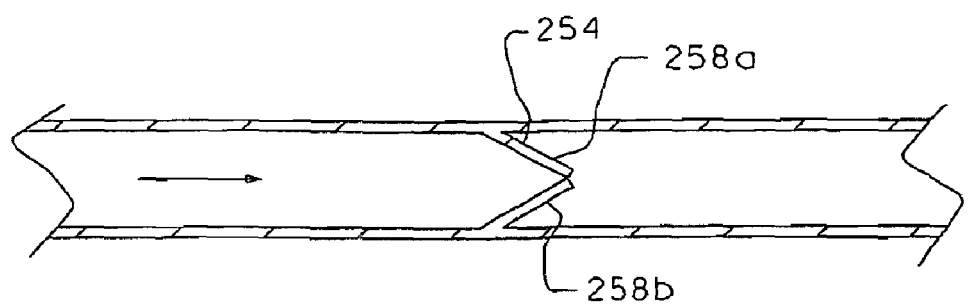
FIG. 4A shows fragmented, side cross-sectional view of another embodiment of an occluder and infusion set with the occluder in a closed configuration.
Figure 4B:
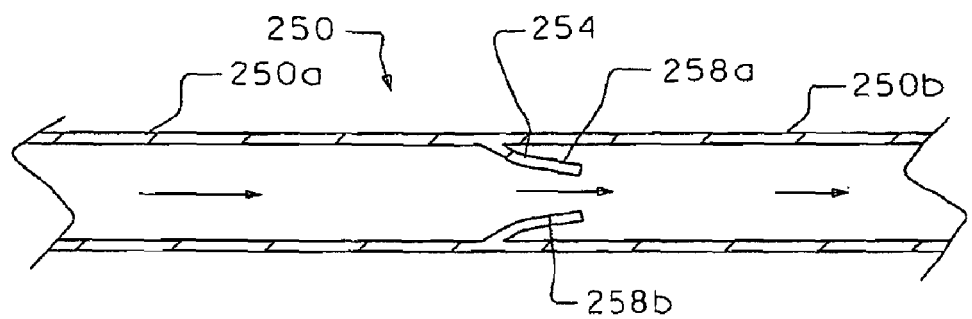
FIG. 4B shows a cross-sectional view of the embodiment of FIG. 4A in an open configuration.

Turning now to FIGS. 4A and 4B, there are shown fragmented, side cross-sectional views of yet another embodiment of the present invention. An infusion set, generally indicated at 250 has an occluder 254 in the form of a duckbill valve formed therein to divide the infusion set 250 into a proximal, upstream portion 250a and a distal, downstream portion 250b. The occluder 254 is formed of two vanes 258a and 258b which are biased into engagement with one another.

When the pressure in the proximal portion 250a of the infusion set 250 is less than about 4 psi, the biasing of the vanes 258a and 258b keep them in contact as shown in FIG. 4A. Once the pressure in the proximal portion 250a exceeds about 4 psi, the pressure forces the valves 258a and 258b away from each other, thereby allowing an infusion liquid to flow through the occluder 254 and into the distal portion 250b of the infusion set 250 as shown in FIG. 4B. In order for the occluder 254 to work in such a manner, it is preferable for the vanes 258a and 258b to extend distally as they engage one another. However, the occluder 254 could be made so that the vanes extend proximally and then buckle once the threshold pressure has been passed.

The occluder 254 is shown as being molded integrally with the infusion set 250. Such a configuration prevents any concern as to whether the occluder 254 may move during use. However, it is feasible to also form such an occluder 254 as a separate unit and then position it within the infusion set 250. The occluder 254 could be held in place with adhesives or merely a friction fit.

Figure 5A:
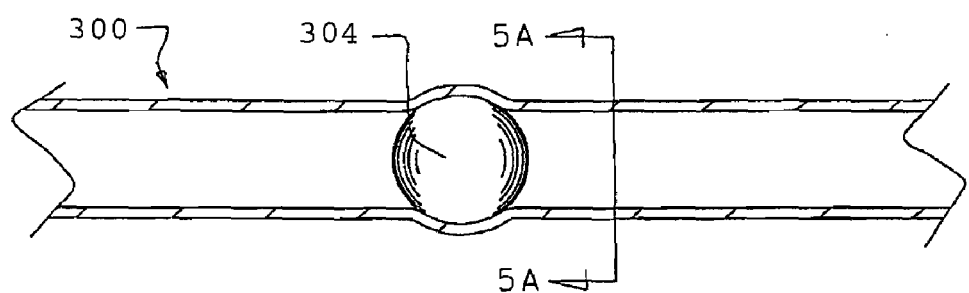
FIG. 5A shows a fragmented side cross-sectional view of an occluder and infusion set made in accordance with one aspect of the present invention with the occluder and infusion set being in a closed position.

Turning now to FIG. 5A there is shown a fragmented, side cross-sectional view of an infusion set, generally indicated at 300, with an occluder 304 disposed therein. Similar to the embodiment shown in FIG. 2A, the infusion set 300 is made of conventional silicone tubing or some other resilient or semi-resilient material, such as latex, polyurethane, etc.

Figure 5B:
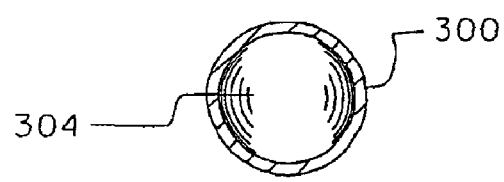
FIG. 5B shows a cross-sectional view taken along plane 5A-5A of FIG. 5A.

FIG. 5B shows an end cross-sectional view of the infusion set 300 and occluder 304 taken along the plane 5A-5A in FIG. 5A. As shown, the tube defining the infusion set 300 forms a seal around the occluder 304 and prevents liquid from passing between the occluder and the tube forming the infusion set.

Figure 5C:
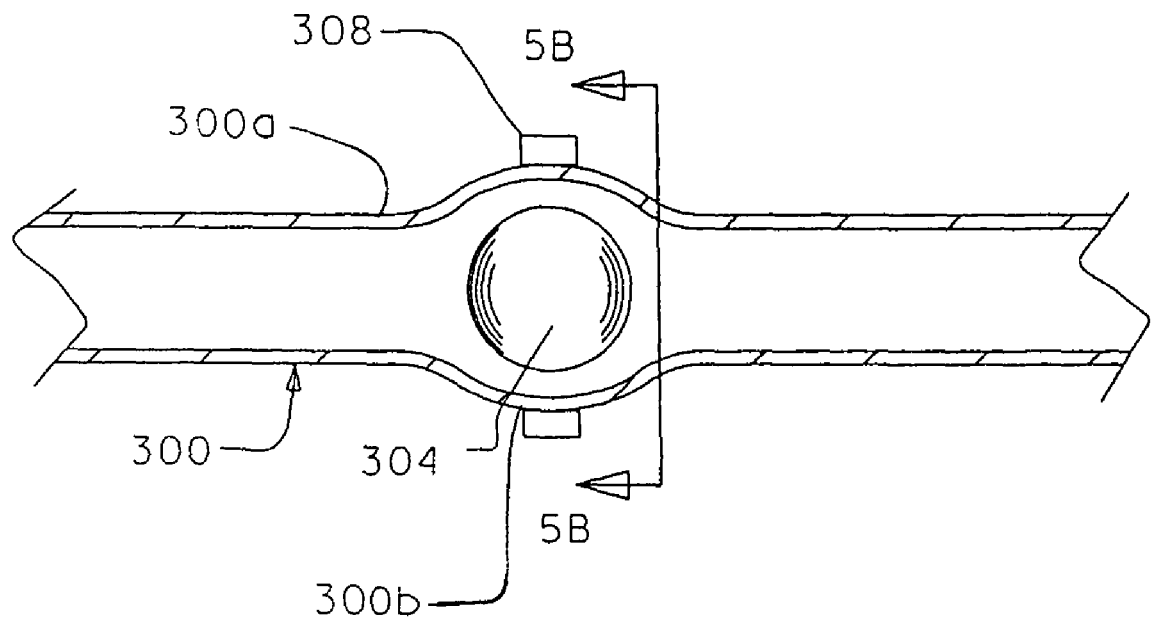
FIG. 5C shows a fragmented, side cross-sectional view of an infusion set with an occluder disposed therein, with the infusion set being mounted in a control mechanism to maintain the infusion set and occluder in an open configuration.

Turning now to FIG. 5C, there is shown a side cross-sectional view of the infusion set 300 and the occluder 304. Disposed behind the infusion set 300 at the location of the occluder 304 is a wall 308. As will be discussed in additional detail below, the wall 308, the occluder 304 and the infusion set 300 form a compression valve for selectively allowing liquid to flow through the infusion set.

Figure 5D:
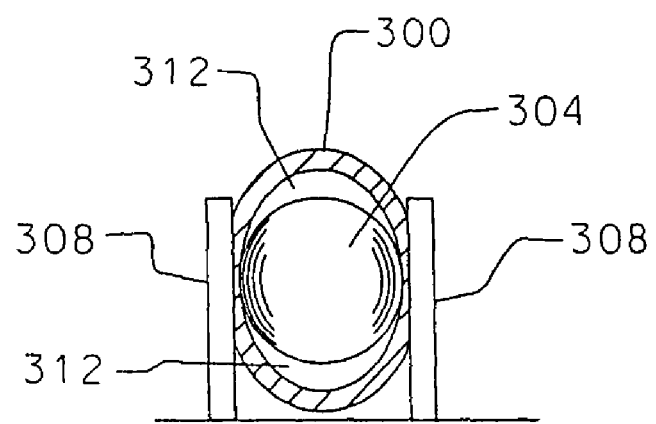
FIG. 5D shows a cross-sectional view taken along the plane 5B-5B of FIG. 5C.

FIG. 5D shows a cross-sectional view of the infusion set 300 and the occluder 304 taken along the plane 5B-5B in FIG. 5C. The infusion set 300 and occluder 304 have been mounted between opposing walls 308 which are spaced apart a distance slightly smaller than the outer diameter of the infusion set. As the infusion set 300 is placed between the opposing walls 308, the sides of the tubing forming the infusion set are compressed and held against the occluder 304. This compression also causes the top and bottom 300a and 300b portions of the tube to extend radially outwardly from the occluder 304, thereby opening a flow path 312 above and below the occluder. The flow paths 312 enable liquid in the infusion set 300 to flow around the occluder 304 and to flow to the patient.

In the event that the infusion set 300 and occluder 304 are pulled out from between the opposing walls 308, the tube forming the infusion set 300 will return to the position shown in FIGS. 5A and 5B, thereby terminating flow through the infusion set. Thus, the configuration shown in FIGS. 5A through 5D prevents free flow of infusion liquids through the infusion set 300 so long as the infusion set and occluder 304 are properly mounted between the walls 308 (or some analogous engagement surfaces). The infusion set 300 and occluder 304 are typically positioned between the walls 308 as the infusion set is being loaded into the pump (not shown). Once properly loaded, the pump controls flow through the infusion set 300 and prevents free flow.

Figure 5E:
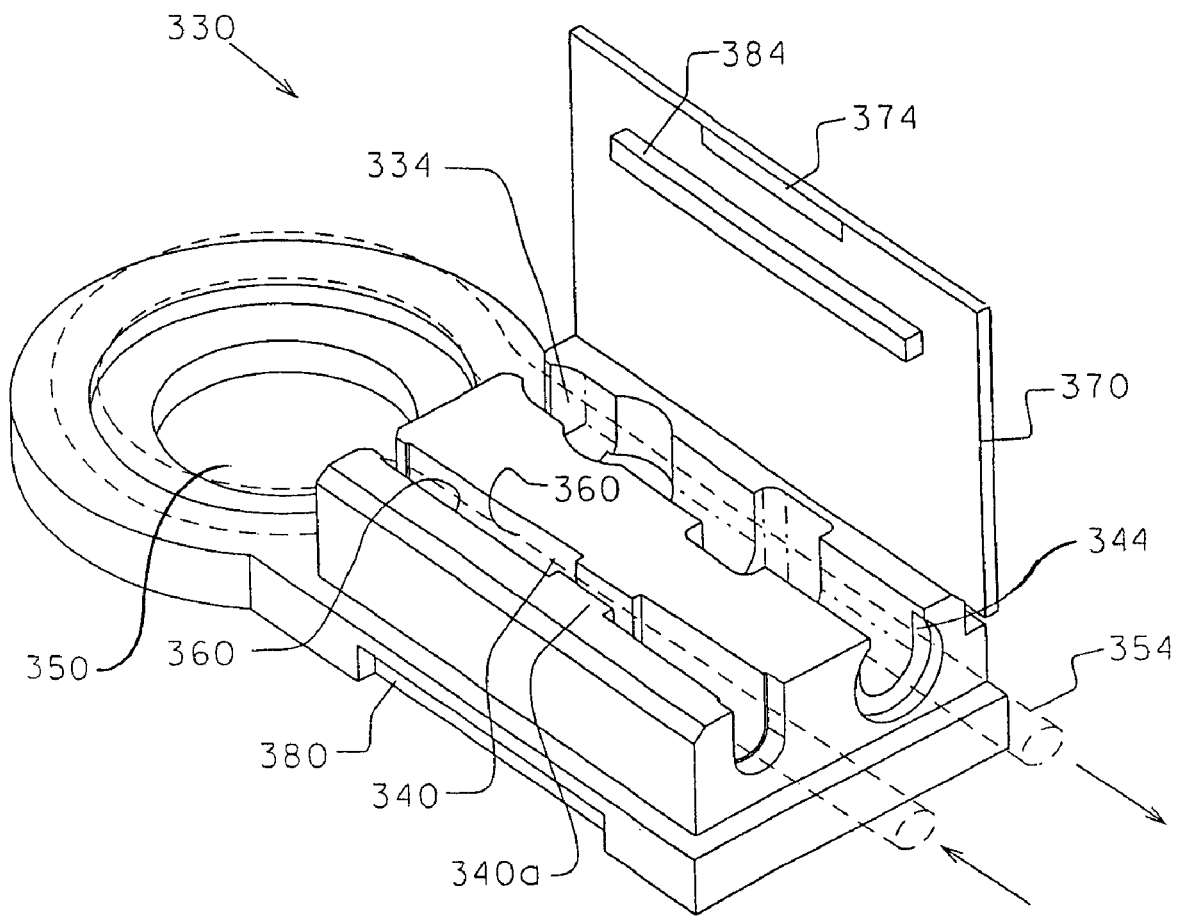
FIG. 5E shows a perspective view of a housing of a control mechanism as may be used to hold the infusion set and occluder in an open position as shown in FIG. 5D.

Turning now to FIG. 5E, there is shown a perspective view of a housing of an enteral feeding pump, generally indicated at 330, made in accordance with one aspect of the present invention. The housing 330 includes a pair of channels 340 and 344 for holding a portion of an infusion set tube, such as those discussed with respect to FIGS. 3A through 5D. In use, the tube is placed in one channel 340, wrapped about a motor unit (not shown) which is placed in the opening 350, and then positioned in the second channel 344. If a conventional infusion set is not properly wrapped about the motor unit (or properly installed in other types of pumps) and placed in the channels 340 and 344, a free-flow condition may develop. However, the present invention prevents such a situation from developing.

As shown in FIG. 5E in broken lines, the infusion set 354 is mounted in the first and second channels 340 and 344. At least a portion 340a of the channel 340 is sufficiently narrow to form walls, similar to walls 308 in FIGS. 5A through 5D, which compress the sides of the tube forming the infusion set 354, thereby creating a flow path around the occluder (not shown) in the infusion set. If desired, the entire length of the walls 360 which form the channel 340 could be sufficiently close together to compress the infusion set 354 and thereby open flow.

FIG. 5E also shows a cover 370 which is connected to the housing 330. The cover 370 is pivotable with respect to the housing 330 and includes a catch 374 which engages a groove 380 on the housing. When the cover 370 is closed and the catch 374 engaged in the groove 380, the infusion set 354 is securely held in the housing 330 and it is unlikely that the infusion set may be pulled from the pump.

Rather than having the walls 360 of the channel 344 compress the sides of the infusion set 354 to form a compression valve with the sides of the infusion set 354, a projection 384 can be mounted on the cover 370 so that it is in alignment with the infusion set. When the cover closes, the projection 384 applies a downward force on the infusion set 354 thereby forming an open compression valve with the flow channels being disposed in horizontal alignment, rather than vertical alignment as shown in FIG. 5D. Thus, liquid flowing through the infusion set 354 passes around the sides of the occluder, as opposed to above and below the occluder.

It will be appreciated in light of the present disclosure, that when a projection is used to engage the occluder, the occluder need not be held in a channel. Rather, the infusion set 354 must only be engaged on generally opposing sides so as to open at least one flow path around the occluder, or sufficient pressure must be exerted to cause the infusion set to expand and open a flow path.

As long as the catch 374 on the cover 370 engages the groove 380 on the housing 330, or the projection 384 is maintained in engagement with the infusion set 354 at the location of the occluder, the compression valve will remain open. If the cover 370 is opened, the force holding the compression valve open is gone and the infusion set 354 will retract into the closed position shown in FIGS. 5A and 5B, thereby preventing free flow through the infusion set 354.

Figure 6A:
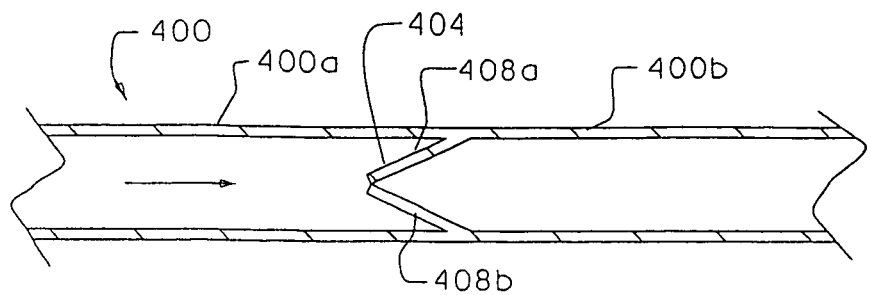
FIG. 6A shows a fragmented, side cross-sectional view of an infusion set having an occluder formed therein in accordance with an aspect of the present invention.
Figure 6B:
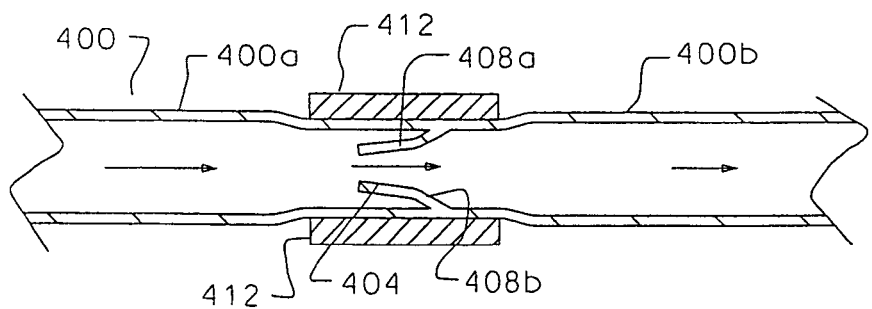
FIG. 6B shows a view similar to that shown in FIG. 6A with the occluder held in an open position.

Turning now to FIGS. 6A and 6B, there is shown yet another embodiment of the present invention. The infusion set, generally indicated at 400, has an occluder 404 disposed therein. The occluder 404 may be molded in the infusion set 400, or may be constructed separately and inserted.

The occluder 404 is formed by a first vane 408a and second vane 408b which form a duck-bill valve. The vanes 408a and 408b are disposed so that they extend proximally (i.e. upstream). As shown in FIG. 6A, the vanes 408a and 408b normally engage one other to occlude flow from a proximal portion 400a of the infusion set 400 to a distal portion 400b of the infusion set.

When pressure is applied to the tubing which forms the infusion set 400, the vanes 408a and 408b move away from each other sufficiently to allow fluid flow through the infusion set. Thus, in FIG. 6B, a compression valve is formed by sliding the infusion set 400 between two walls 412 of engagement surfaces so that the vanes 408a and 408b are held apart, or by forcefully engaging the infusion set with a projection or other structure associated with a door, etc. As long as the infusion set 400 remains between the walls 412, projections, etc., fluid flow is enabled. If the portion of the infusion set 400 which contains the occluder 404 is pulled from the walls 412 or projections, the occluder will return to the closed position wherein it prevents free flow.

Preferably, the infusion set 400 and occluder 404 will be used in a housing, such as that shown in FIG. 5E. When the infusion set 400 is mounted in a channel defined by restricting sidewalls or when a cover with an aligned projection is closed, flow is enabled through the infusion set. If the infusion set 400 is pulled out of the housing, the occluder 404 will automatically close—thereby preventing free flow through the infusion set.

The various embodiments disclosed in accordance with the present invention provide a marked improvement over clamps and other types of external occluders which are commonly used to control fluid flow. These embodiments provide assurance against free flow, are generally easier to handle and are much more cost effective than the external occluders of the prior art.

In addition to being usable with housings and other fixed structures which cause the valve to open, the majority of configurations discussed above can also be manually opened by simply squeezing the infusion set adjacent the occluder to open a pathway around the occluder. The availability to manually open the occluder/infusion set is desirable, as it facilitates priming of the infusion set with the liquid being infused. Unlike many of the occluders of the prior art however, simply releasing the infusion set adjacent the occluder is all that is required to terminate flow.

Figure 7:
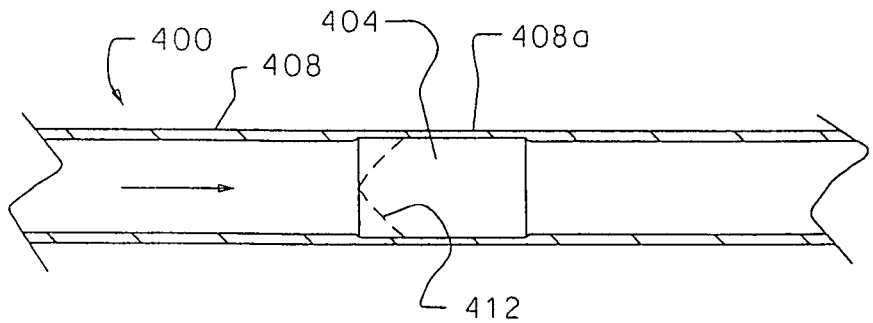
FIG. 7 shows another configuration of an occluder made in accordance with the principles of the present invention.

Turning now to FIG. 7, there is shown another configuration of an infusion set, generally indicated at 400, and an occluder, 404 made in accordance with the principles of the present invention. The infusion set 400 is formed by an elongate tube 108 made of a flexible, resilient material such as silicone rubber, latex, polyurethane, neoprene or numerous similar materials. Typically, the elongate tube has an inner diameter of approximately 0.130 inches.

The occluder 404 has an exterior diameter which is slightly larger than the interior diameter of the tube forming the infusion set 400, typically about 0.141 inches. This causes a portion 408a of the tube to stretch slightly as it passes over the occluder 404.

The occluder 404 prevents flow through the infusion set 400 based on gravity. Thus, the exact size of the occluder 404 will depend on the material used to form the infusion set 400. In a presently preferred embodiment, the infusion set 400 is formed from a tube made of silicone rubber, and the occluder 404 is formed from a plastic (e.g. acrylonitrile butyl styrene (ABS), acrylic (PMMA), polycarbonate, etc.) cylinder having an outer diameter of 0.141 inches and a length of about 0.282 inches.

Because the occluder 404 is larger than the interior diameter of the infusion set 400, solution which is under only the force of gravity will back-up behind the occluder and not pass. Once sufficient pressure is present—e.g. pressure produced by a pump—the walls of the infusion set will expand to allow fluid flow past the occluder 400 as discussed with respect to FIG. 2A, etc.

While the embodiment shown in FIG. 2A is spherical and the embodiment shown in FIG. 7 is cylindrical, those skilled in the art will appreciate that numerous other embodiments could be used. For example, the dashed line 412 illustrates an occluder which is bullet shaped. Occluders can also be egg shaped, or any other shape which provides a stop to fluid flow until a predetermined pressure threshold has been reached. It will also be appreciated that the occluder 404 need not have a consistent diameter. By having a portion of the occluder 404 extend radially a greater distance than other parts, a portion of the occluder will always engage the wall of the infusion set 400, thereby reducing the ability of the occluder to move within the infusion set.

Figure 8:
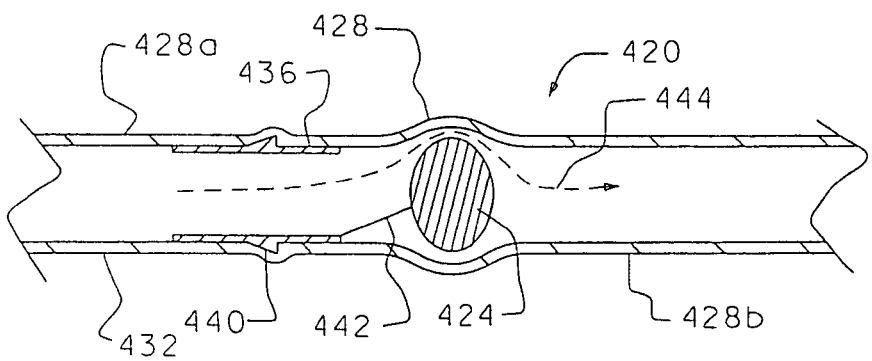
FIG. 8 shows yet another configuration of an occluder made in accordance with the principles of the present invention.

Turning now to FIG. 8, there is shown still another configuration of an infusion set 420 and occluder 424 made in accordance with the principles of the present invention. The infusion set 420 is formed from an elongate tube 428 which has a first portion 432 and a second portion 436 which are connected together by a connector 440. The occluder 424 is attached to the connector 440 by a tether 442 to prevent the occluder from advancing along the second portion 436 of the elongate tube 428.

When sufficient pressure is present in a proximal, upstream portion 428a of the elongate tube 428, the second portion 432 will expand sufficiently to allow fluid flow past the occluder 424 and into the distal, downstream portion 428b of the infusion set 420. One advantage of using the connector is that the first portion 428a of the elongate tube 428 need not be formed of a material which is resilient, or may use a material which does not expand or contract consistently. In other words, less expensive tubing materials may be used for most of the infusion set 420 without interfering with the interaction between the infusion set and the occluder 424.

While shown in FIG. 8 as being generally spherical, it should be appreciated that, in accordance with the present invention, the occluder 424 could be a variety of shapes. Additionally, a single tether 442 or a plurality of tethers could be used to hold the occluder 424 to the connector 440.

Figure 8A:
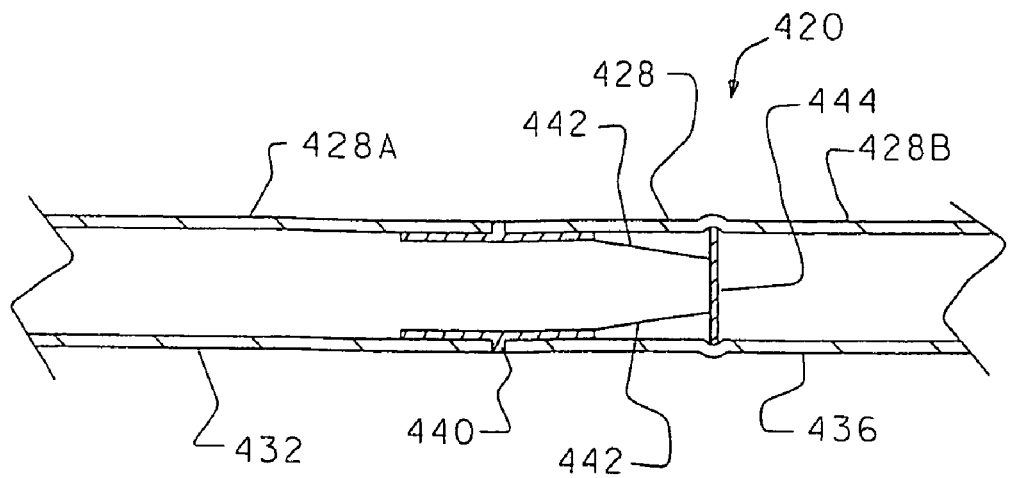
FIG. 8A shows a cross-sectional view of another configuration of an occluder in accordance with the present invention.

FIG. 8A shows a cross-sectional view of another configuration of an infusion set 420, and an occluder 444. Unlike the spherical occluder 424 of FIG. 8, the occluder 444 of FIG. 8A is disk shaped. To prevent the occluder 444 from rotating in response to fluid pressure and inadvertently opening a fluid flow path, a plurality of tethers 442 are used to secure the disk to the connector 440.

When pressure in the infusion set 420 is sufficient, the tube 428 will expand and allow fluid flow past the occluder 444. Once the pressure drops below a predetermined threshold, the tube 428 will again engage the occluder 444 and terminate flow.

Figure 8B:
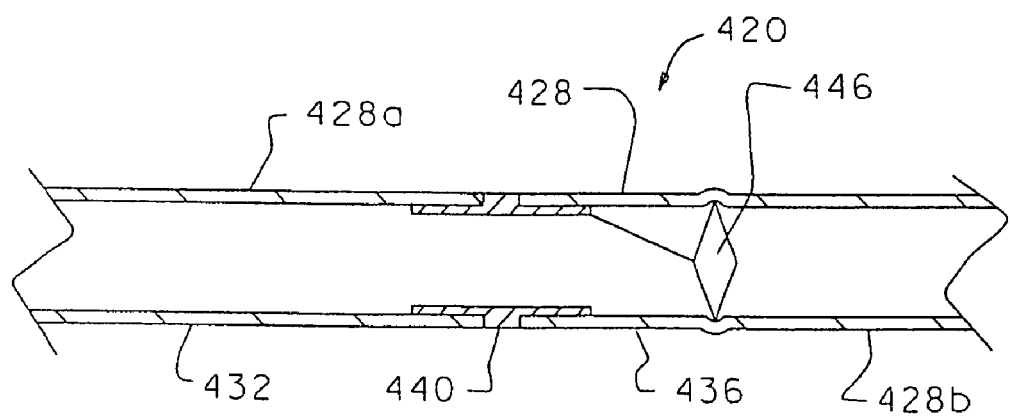
FIG. 8B shows a cross-sectional view of still yet another configuration of an occluder in accordance with the present invention.

FIG. 8B shows a cross-sectional view of still yet another configuration of an occluder, 446, made in accordance with the principles of the present invention. The infusion set 420 and related portions are the same as in FIGS. 8 and 8A and are numbered accordingly.

The connector 440 is attached by one or more tethers 442 to the occluder 446 to prevent the occluder from moving down stream. The tethers 442 can also be used to keep the occluder 446 in a desired orientation. When sufficient pressure is present, the tube 436 expands to allow fluid flow past the occluder 446.

Figure 9:
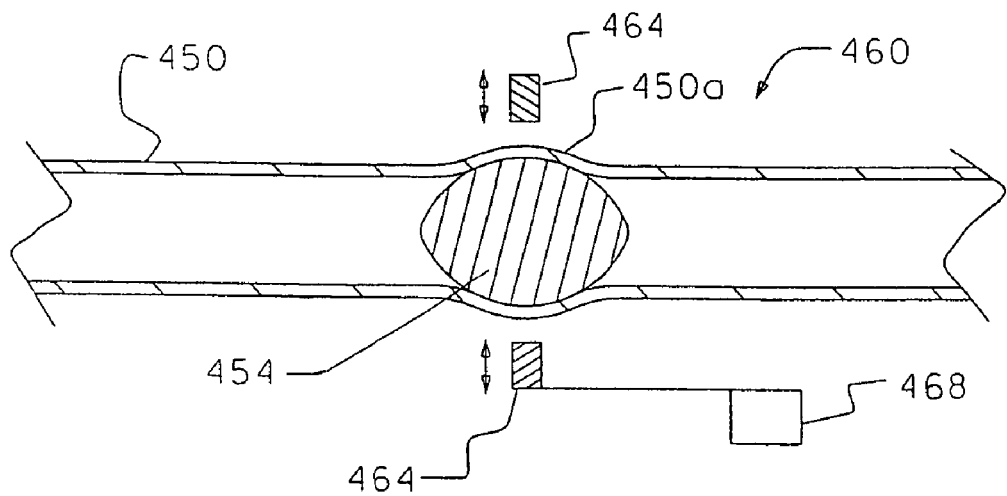
FIG. 9 shows yet another aspect of the invention wherein the occluder forms part of a liquid control valve.

FIG. 9 shows yet another aspect of the invention wherein the infusion set 450 and occluder 454 forms part of a liquid control valve, generally indicated at 460. In accordance with the embodiments discussed above, and particularly the discussion surrounding 5A through 5E, the occluder 454 normally prevents fluid flow through the infusion set. However, squeezing the infusion set on opposing sides of the infusion set sidewall 450a caused other portions of the sidewall to extend away from the occluder 454—as demonstrated in FIGS. 5C and 5D.

Disposed adjacent to the infusion set 450 and occluder 454 are a pair of engagement members 464 which are in communication with an actuator 468, such as a motor. The communication can be electronic, mechanical or pneumatic, so long as the actuator 468 is able to control movement of one or more of the engagement members 464.

When the engagement members are actuated, they apply an inward force to the infusion set 450 at the location of the occluder 454 to open a passage way around the occluder and thereby enable fluid flow through the infusion set. When the engagement members 464 are adjusted to no longer apply sufficient force to the infusion set 450, the infusion set again surrounds the occluder 454 and prevents fluid flow.

By selectively actuating the engagement members 464, the infusion set 450 and occluder 454, a valve is formed for controlling fluid flow. By applying a pressure sensor or other type of sensor, the valve can be used to regulate flow and flow through the valve can be determined.

Figure 10:
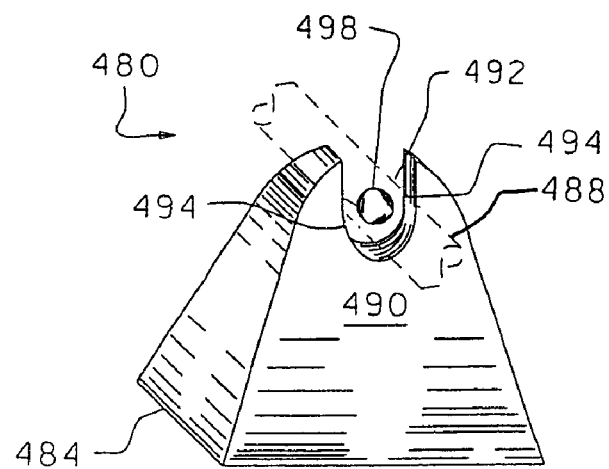
FIG. 10 shows a perspective view of a clip for retrofitting existing pumps for use with an occluder of the present invention.

Turning now to FIG. 10, there is shown a perspective view of a clip, generally indicated at 480, for opening flow between an occluder and infusion set. Those skilled in the art will appreciate that there are a number of enteral and parenteral pumps in the market which use various types of occluders which suffer from the problems identified in the background section. To eliminate these concerns, the clip 480 is configured for retrofitting an existing pump for use with an occluder/infusion set made in accordance with the principles of the present invention. (Of course, with some existing pumps, the occluder and infusion set may be configured to nest in the pump in such a manner that retrofitting is not necessary.)

The clip 480 includes a base 484 which is provided for attachment to the housing of a conventional fluid pump. Typically, the base 484 will have an adhesive disposed thereon. If desired, the adhesive may be selected from removable adhesives, such as those known to those skilled in the art, so that the clip 480 can be removed from the pump when an infusion set containing an occluder (such as that represented by the dashed lines 488) is not being used with the pump.

Extending from the base 484 is a fitting 490 having channel 492 formed therein. The channel 492 is preferably formed with an open end and extends into the clip 480. As the infusion set, represented in shadow at 488, is inserted into the channel 492, walls 494 defining the channel compress the infusion set 488 against the occluder (shown as dashed lines 498) to open a pair of flow channels between the occluder and the infusion set as shown in FIGS. 5A through 5D.

As long as the infusion set 488 and occluder 498 remain securely held between the walls 494 defining the channel 492, fluid flow is enabled between the occluder and the infusion set. If the infusion set 488 is pulled from the channel 492 or is never properly placed in the channel, flow through the infusion set is prevented. Thus, the risk of free flow developing within the system is significantly reduced. Of course, the risk of free flow can virtually be eliminated by placing the clip 480 on the pump in such a manner that the infusion set 488 must be properly loaded in the pump in order to fit within the channel 492.

Figure 11:
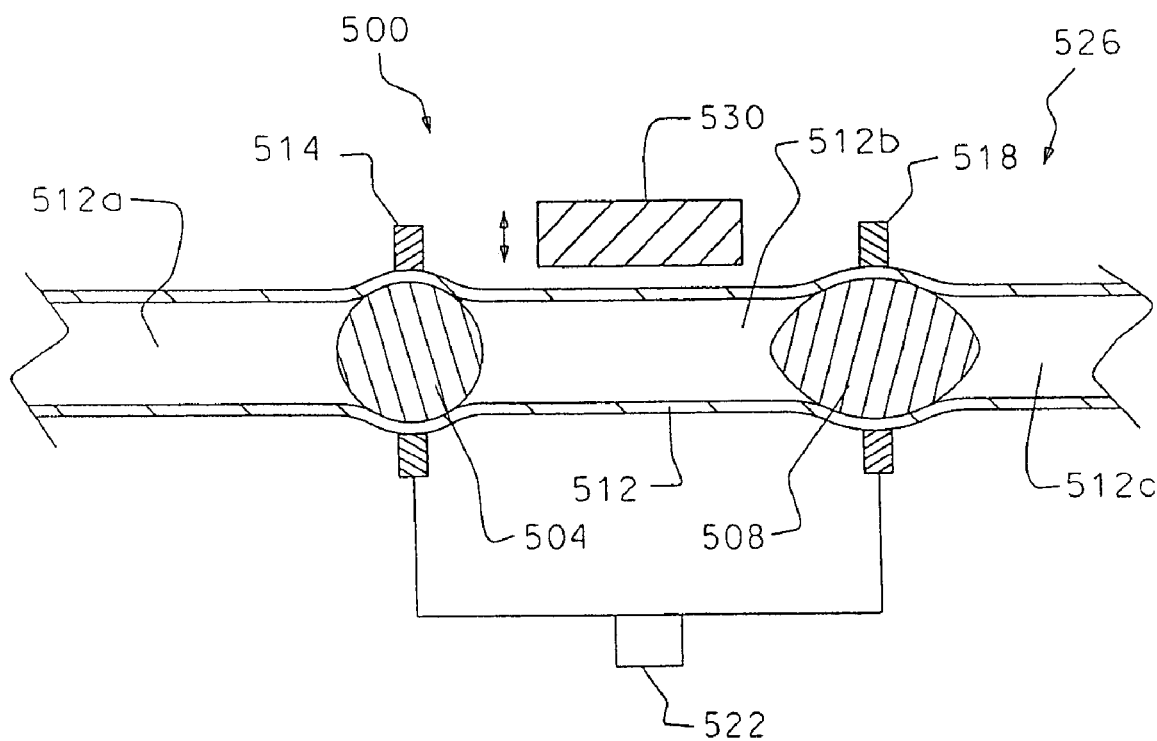
FIG. 11 shows a side cross-sectional view of a pair of occluders and infusion line which form a pair of valves, and a force applicator to form a linear peristaltic pump.

FIG. 11 shows a side cross-sectional view of yet another embodiment of the present invention which forms an in-line pump, generally indicated at 500. As shown in FIG. 11, a pair of occluders 504 and 508 are disposed in an infusion line 512. Each of the occluders 504 and 508 is disposed adjacent an actuator 514 and 518, respectively. The actuators 514 and 518 are configured to selectively apply pressure to the infusion line 512 to selectively open flow channels between the infusion line and the occluder 504 or 508 with which each is associated.

In use, liquid in the infusion line 512 will be held in a proximal portion 512a which is upstream from the first occluder 504. The first occluder 504 prevents the liquid from flowing down stream until a drive mechanism 522 causes the first actuator 514 to apply force to the infusion line 512 adjacent the first occluder. Applying force to the infusion line 512 causes a channel to open between the first occluder 504 and the infusion line, thereby allowing fluid flow into a middle portion 512b of the infusion line.

Once the middle portion 512b of the infusion line 512 has had adequate time to fill with liquid, the actuator 514 is adjusted so that it no longer applies sufficient force to the infusion line to enable fluid flow around the occluder 504. The liquid in the middle portion 512b of the infusion line 512 is then isolated from the liquid in the proximal portion 512a.

The liquid in the middle portion 512b of the infusion line 512 is prevented from flowing distally or downstream by the second occluder 508 which defines the distal end of the middle portion. However, once the drive mechanism 522 is actuated to move the actuator 518 into forceful contact with the infusion line 512 adjacent the occluder 508, one or more channels are formed between the occluder and the infusion line. The channel(s) opened by the actuator 518 squeezing the infusion line 512 form a flow path allowing the liquid contained in the middle portion 512b to flow into a distal, downstream portion 512c. Since no occluder or other stop is typically disposed distally from the second occluder 508, the liquid flowing into the distal portion 512c is delivered to the patient.

By selectively controlling the application of force by the first actuator 514 on the infusion line 512 and first occluder 504 and the application of force by the second actuator on the infusion line and second occluder 508, a valve, generally indicated at 526, is formed which permits a predetermined amount of flow to pass with each series of actuations.

In a more preferred embodiment, the valve also includes a force applicator 530, such as a plunger, roller or similar device, disposed in communication with the middle portion 512b of the infusion line 512. The force applicator 530 applies a compressive force to the middle portion 512b of the infusion line 512 to force the liquid contained in the middle portion 512b to flow into the distal portion 512c of the infusion line 512 and on to the patient. The force applicator 530 ensures that liquid will not simply remain in the middle portion 512b when the second actuator 518 causes a flow path to be formed between the second occluder 508 and the infusion line 512.

While applying a compressive force to the middle portion 512b of the infusion line 512 helps to force the liquid in the middle portion to flow downstream, it also serves to assist flow into the middle portion. Once a compressive force is no longer applied to the middle portion 512b, the resilient material forming the infusion line will attempt to return to its original, tubular configuration. By closing the flow path between the second occluder 508 and the infusion line 512 before releasing force applicator 530, a vacuum is formed within the middle portion 512b. Once the actuator 514 opens a flow path between the first occluder 504 and the infusion line 512, the vacuum in the middle portion 512b will draw liquid into the middle portion 512b as the infusion line returns to its original configuration.

In each cycle of the valve 526, the first actuator 514 will open a flow channel between the first occluder 504 and the infusion line 512 to fill the middle portion 512b with liquid. The first actuator 514 will then allow the flow channel to close. The second actuator 518 will then open a flow channel between the second actuator 508 and the infusion line 512 and the force applicator 530 will apply pressure to the infusion line forming the middle portion 512b so that the liquid in the middle portion will flow into the distal portion 512c and to the patient. The second actuator 518 will then allow the flow channel between the second occluder 508 and the infusion line 512 to close. The process will then be repeated.

By controlling the interior diameter of the infusion line 512, the distance between the first occluder 504 and the second occluder 508, and the movement/size of the force applicator 530, one can obtain a predetermined amount of liquid flow with each cycling of the valve 526. By controlling the number of cycles in a predetermined period of time, the operator is able to provide a highly accurate rate of flow for the solution passing through the valve 526. Furthermore, because a rotor is not needed to control flow rate, the valve 526 can be used to make an in-line peristaltic pump which is significantly thinner than conventional peristaltic pumps while maintaining the same accuracy.

While FIG. 11 shows two actuators, those skilled in the art will understand, in light of the present invention, that one of the occluders could be configured to allow fluid flow responsive to force if configured properly to prevent back flow. This could be achieved, for example, by controlling the size of the occluders.

Figure 12A:
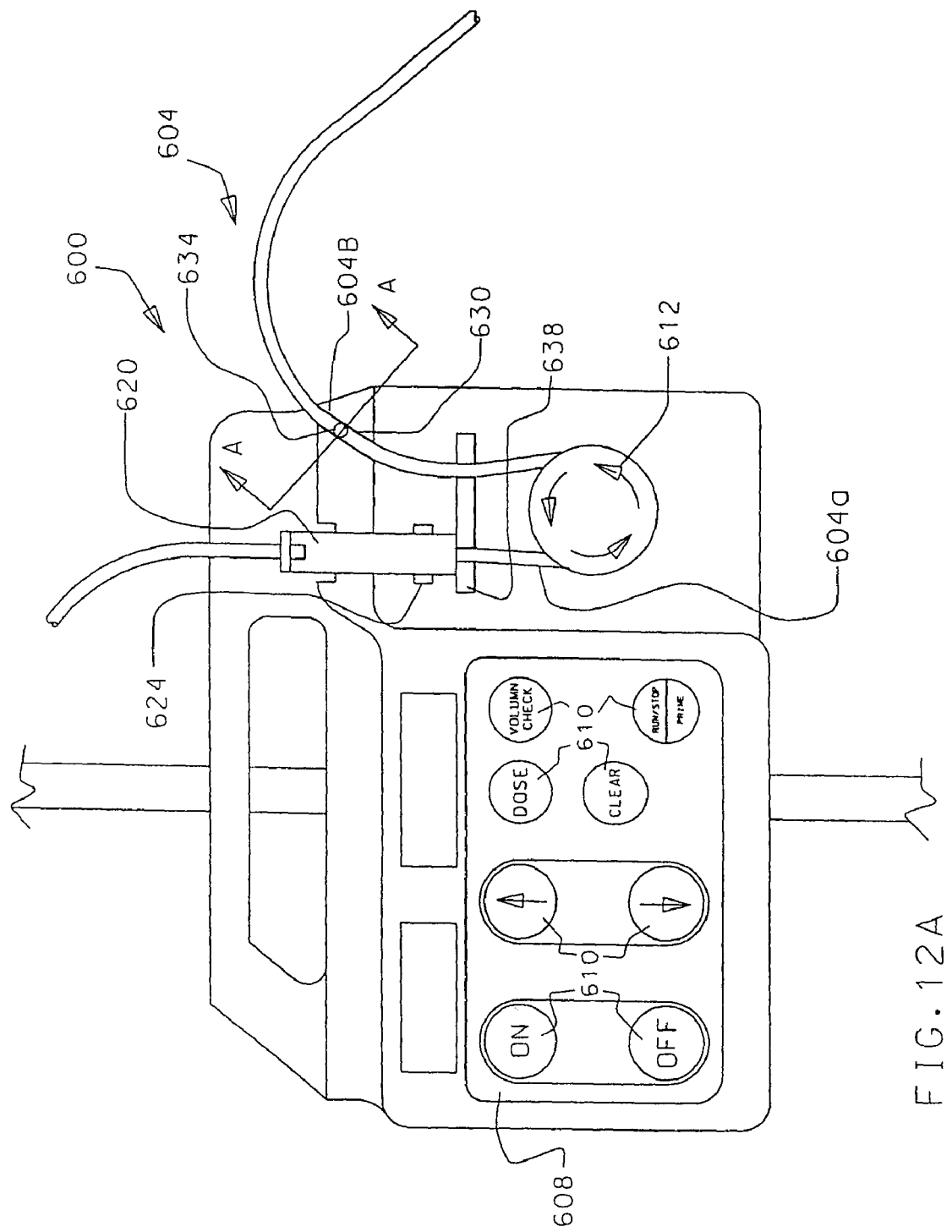
FIG. 12A shows a front view of an enteral feeding pump of the prior art with an occluder in accordance with the present invention disposed therein.

Turning now to FIG. 12A, there is shown a perspective view of a pump, generally indicated at 600, which is designed to control fluid flow through an infusion set, generally indicated at 604, and into the patient. The pump 600 includes a control panel 608 which has a plurality of buttons 610 or other devices for controlling the actuation of the pump. The pump 600 operates to deliver a predetermined dose of enteral feeding solution to a patient by rotation of a rotor 612.

The infusion set 604 is mounted on the pump so that a resilient portion 604a of the infusion set wraps around the rotor 612. A bracket 638 may be used to secure the infusion set 604, 604a, the drip chamber 620, etc. Each rotation or partial rotation of the rotor 612 causes a predetermined amount of enteral feeding solution to be advanced through the infusion set 604 and delivered to the patient.

In order to assure that the rotor 604 is providing the proper amount of enteral feeding solution, a drip chamber 620 is formed along the infusion set. An optical sensor 624 is disposed in the enteral feeding pump 600 and monitors the drip rate of the solution in the drip chamber 624. The drip rate of the solution is used to calculate an actual delivery rate of the solution.

As with the prior art, a portion 604b of the infusion set disposed distally from the rotor 612 is nested in a channel 630 in the pump housing 600. In accordance with the present invention, the portion 604b has an occluder 634 disposed therein. While the prior art simply used the channel 630 to hold the infusion set 604 in contact with the rotors, the inclusion of an occluder 634 provides an improved measure of safety.

In the prior art, if either the portion 604b of the infusion set 604 was not properly positioned in the channel 630, a free flow condition could develop in which fluid flow through the infusion set would be unchecked by the rotor 612. In the present invention, flow through the infusion set 604 is not permitted until the portion 604b with the occluder 634 is nested in the channel 630. If the portion 604b of the infusion set 604 is not properly placed in the channel 630 or is pulled from the channel, the occluder 630 will prevent free flow through the infusion set.

Figure 12B:
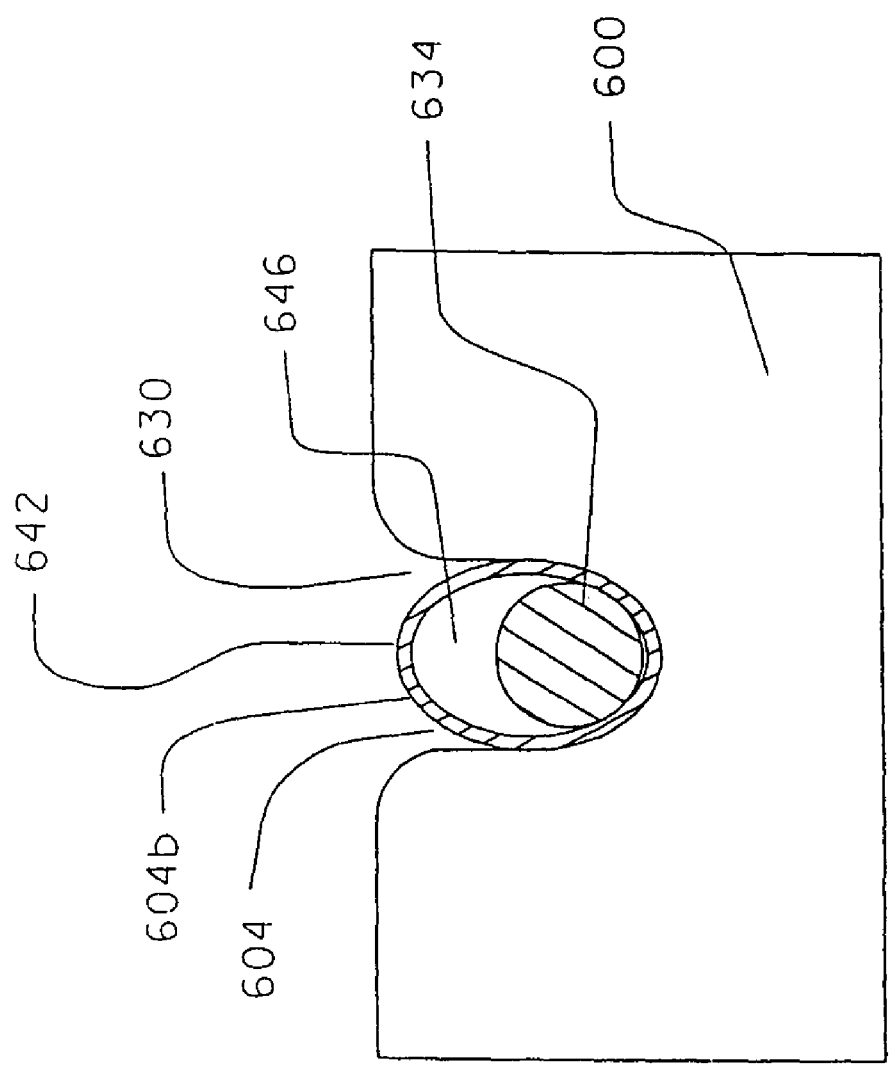
FIG. 12B shows a close-up, cross-sectional view of the occluder disposed in tubing of an infusion set and a portion of the pump to demonstrate opening of a fluid flow pathway around the occluder.

FIG. 12B shows a close-up, cross-sectional view of the portion of the pump 600 having the channel 630 formed therein taken along the line A-A. The channel 630 receives the infusion set 604 in such a manner that it compresses the tube 642 against the occluder 634. This causes another portion of the tube 642 to extend away from the occluder 634 and thereby open a fluid flow path between the inner wall of the tube and the occluder.

As shown in FIG. 5D, compressing opposing sides of the infusion set can open fluid flow channels both above and below the occluder. In FIG. 12B, the tube 642 of the infusion set 604 is pressed against one half of the occluder 634, thereby forming a single fluid flow channel 646 on the opposing side. If the portion 604b of the infusion set 604 containing the occluder 634 is pulled from the channel 630, the infusion set will engage the occluder and prevent fluid flow.

Figure 13A:
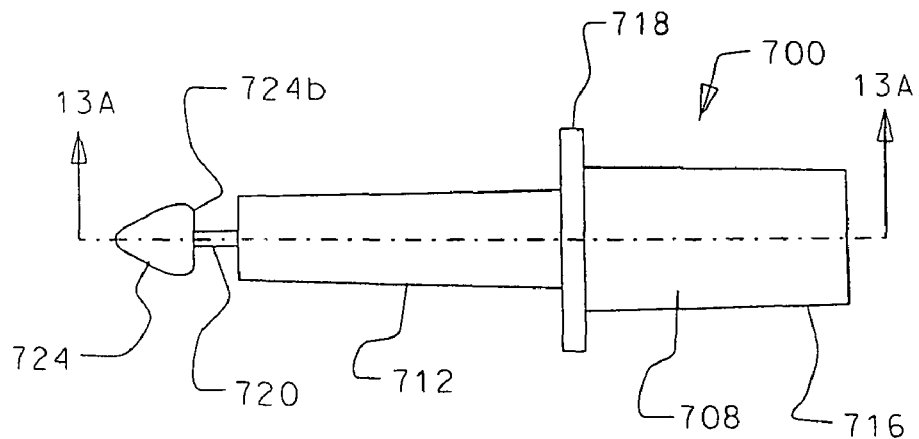
FIG. 13A shows a side view of an alternate embodiment of an occluder made in accordance with the principles of the present invention.

Turning now to FIG. 13A, there is shown a connector having still another embodiment of the present invention. The connector 700 is formed by an adaptor body 708 which is used to connect two pieces of tubing together. Most commonly, the adaptor body 708 is used to connect a silicone tube segment which engages the pump rotor, to the remaining tubing of an infusion set (not shown.) Such connectors 700 are used on a variety of infusion sets currently in use.

The adaptor body 708 is formed by a proximal section 712, a distal section 716, and an annular flange 718 which limits the advancement of tubing along the proximal and/or distal sections of the adaptor body. The proximal section 712 usually engages the silicone tubing, while the distal section 716 engages the remaining tubing of the infusion set.

An arm 720 forming a tether/spacer extends proximally from the proximal portion 712, and holds an occluder 724 a spaced distance from the rest of the adaptor 708. Unlike the prior embodiments discussed above, the occluder 724 is generally tear drop shaped when the adaptor 708 is standing on end. As shown in FIG. 13a, the distal end 724a of the occluder 724 may be squared off. However, it may also be rounded or otherwise contoured. In light of the embodiments discussed above, those skilled in the art will appreciate that a spherical, diamond shape or other shaped occluder could also be used.

Unlike the tether arrangements discussed in previous embodiments, the arm 720 holds the occluder 724 generally rigidly and proximally from the adaptor. In the event the arm 720 were to be broken by improper bending of the infusion set in which the adaptor body 708 is mounted, the occluder 724 would not be able to move down stream in the infusion set. To the contrary, adaptor body 708 would prevent distal movement and the position of the arm and the shape of the occluder 724 would prevent the occluder from completely blocking flow through the tube so long as the designated pressures are being used to properly expand the tube.

Figure 13B:
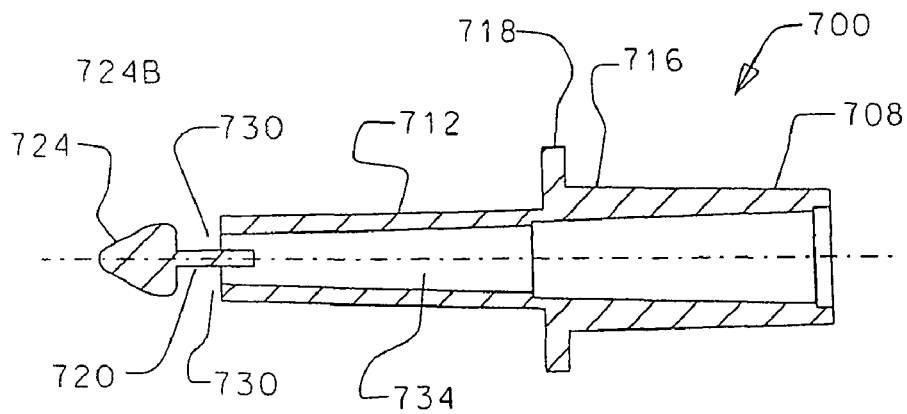
FIG. 13B shows a cross-sectional view of the occluder embodiment of FIG. 13A taken along the line 13A-13A.
Figure 13C:
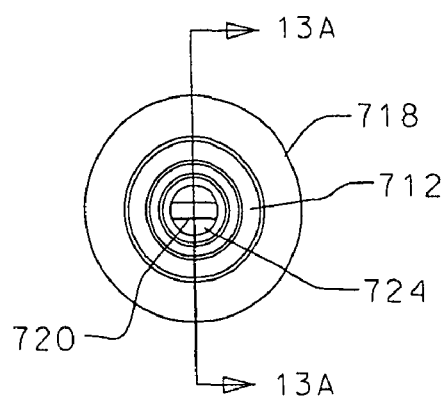
FIG. 13C shows an end view of the occluder of FIGS. 13A and 13B.

Turning now to FIG. 13B, there is shown a cross-sectional view of the connector 700 shown in FIG. 13A. This view demonstrates the two flow channels 730 which are formed on either side of the arm 720. The two flow channels 730 are configured to allow fluid which had flowed passed the occluder 724 to enter the hollow channel 734 of the adaptor body 708 and to flow downstream from the occluder. An end view of the connector 700 is shown in FIG. 13C.

The opening in the proximal end of the proximal section 712 is preferably about 0.098 inches in diameter and is bisected by the arm 720 which is about 0.03 inches thick. The occluder 724 is preferably spaced about 0.085 inches from the proximal section 712, and is provided with a radius of curvature of 0.025 inches on the front end. The rounded portion of the distal end is typically about 0.03 inches long.

The spacing of the occluder 724 from the proximal section 712 and the size of the flow channels 730 are sufficient to allow fluid to flow readily through the connector 700 if the pressure is above about 5 psi. If the pressures are below about 5 psi, the occluder 724 will prevent flow of the fluid through the connector 700.

Having the occluder 724 be formed as part of the connector 700 has several distinct advantages. First, it has been found that the occluder 724 can be formed by molds substantially the same as the molds currently used for such parts. Thus, rather than having to engineer an entirely new product, infusion set manufacturers can readily adapt their molds to add the occluder 724. The cost of adapting the mold is almost negligible. Additionally, the amount of additional plastic used to form the occluder raises the cost of producing the connector 700 by a mere fraction of a cent. This is in contrast to presently available pinch clip occluders and clamps which can cost ten to twenty cents and constitute more than ten percent of the cost of the infusion set. Thus, for almost no cost, the infusion set can be provided with a highly reliable anti-free flow device.

Figure 13D:
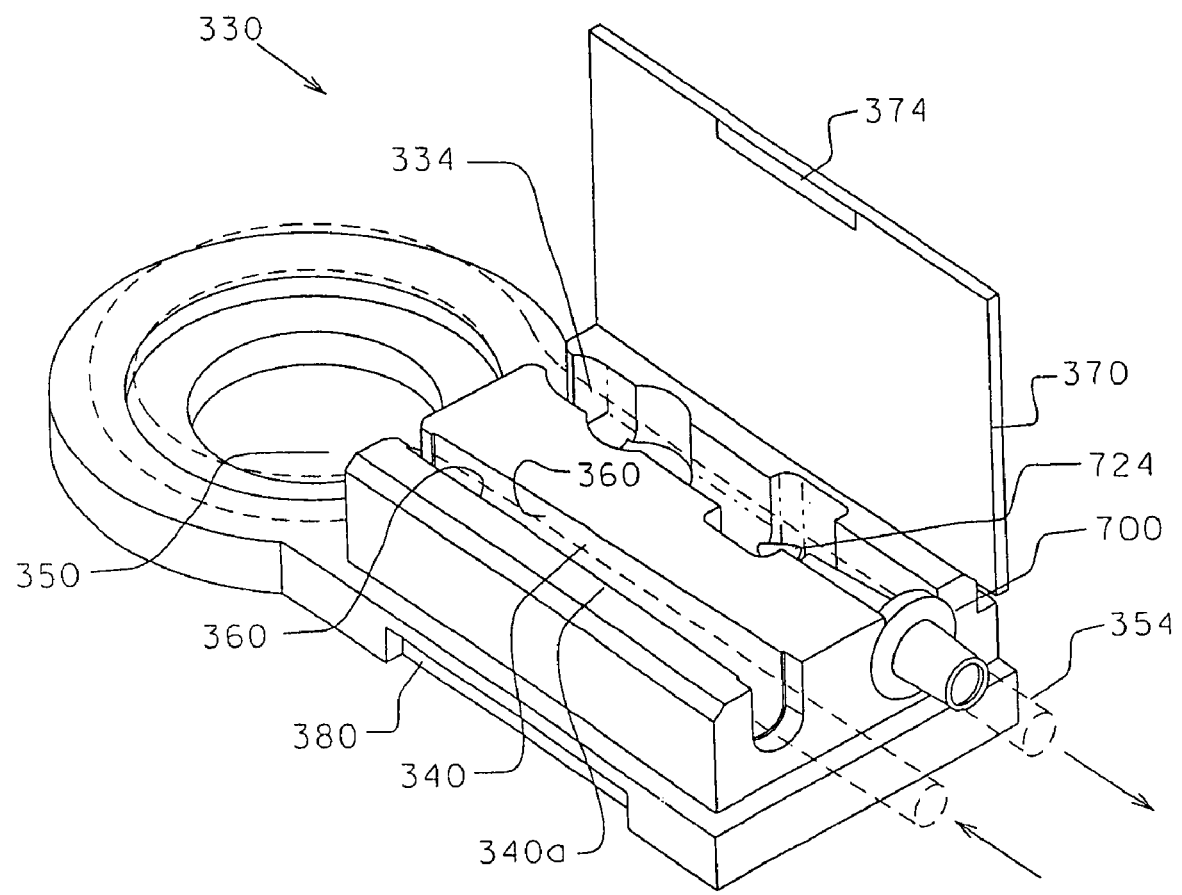
FIG. 13D shows a top view of an enteral feeding pump having an infusion set disposed therein, with an occluder positioned in the infusion set to prevent free-flow therethrough in accordance with the present invention.
Figure 13E:
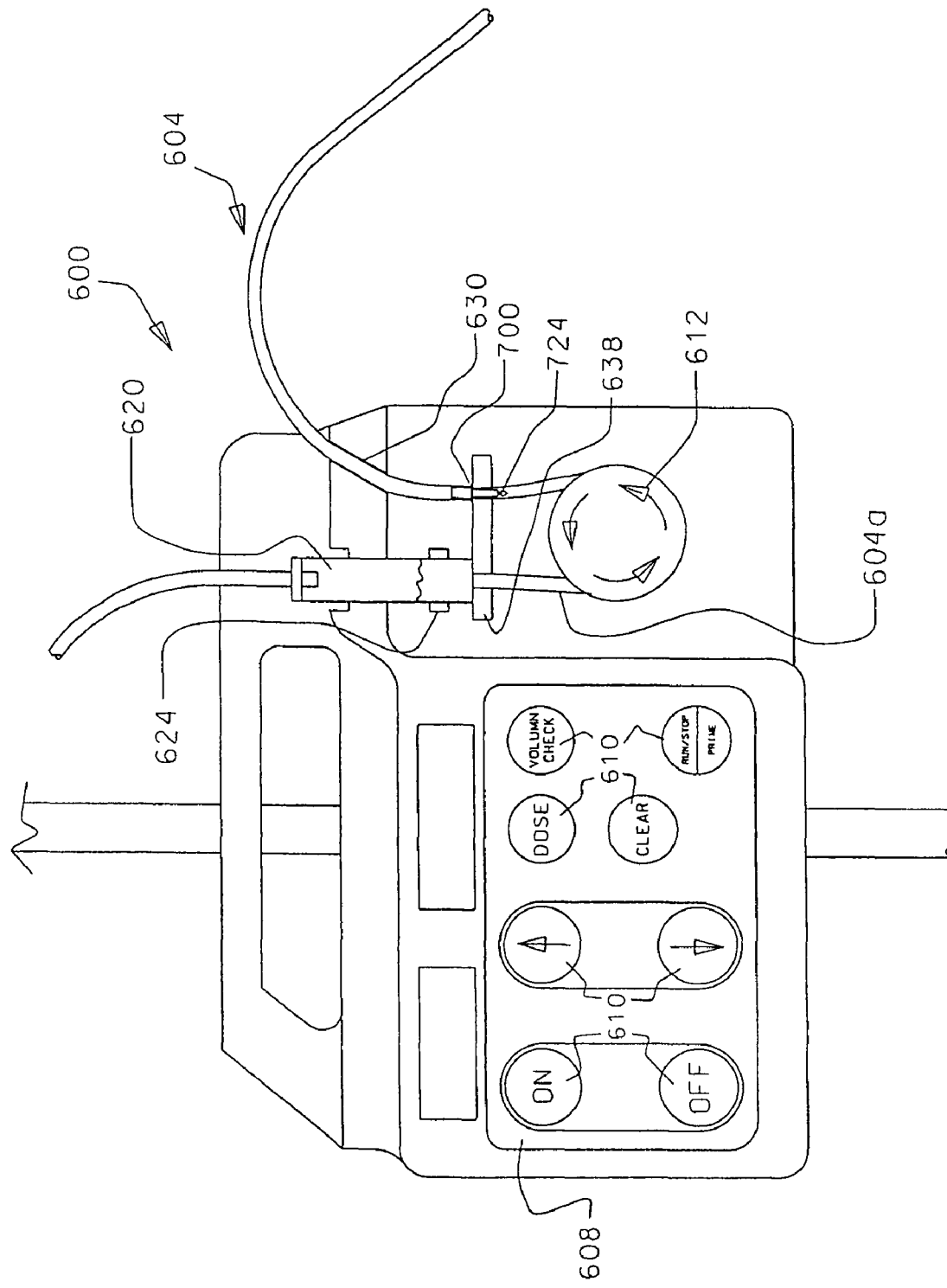
FIG. 13E shows a front view of another available enteral feeding pump having an infusion set disposed therein, with an occluder positioned in the infusion set to prevent free-flow therethrough in accordance with the present invention.

FIGS. 13D and 13E show the pumps discussed in FIGS. 5E and 12A, respectively, but configured for use with an adapter/occluder. To avoid excessive repetition, the portions of the pumps which are similar to those in FIGS. 5E and 12A are labeled according.

As shown in FIGS. 13D and 13E, the connector 700 is preferably mounted to the infusion pump downstream from the pump rotor 750 (FIG. 13D) and 760 (FIG. 13E). As the pump rotor 750/760 rotates, it will create sufficient pressure to cause the fluid being pumped to pass around the occluder 724 and into the channel 734 (FIG. 13B) in the connector 700. The fluid is then free to flow down stream.

The connector 700 is highly advantageous because it can be used on most infusion pumps without the need for retrofitting or otherwise modifying the infusion set. It eliminates the need to recess an occluder as shown at numeral 630/634 in the pump shown in FIG. 12A, and eliminates the need for modified channels 340/340a or a projection 384 as discussed with respect to FIG. 5A. When mounted in the infusion set, the connector 700 appears substantially the same as the conventional connector and the patient may not even know it is being used unless told. However, the advantages of conventional pinch clip occluders, etc., are achieved without the disadvantages.

Figure 14A:
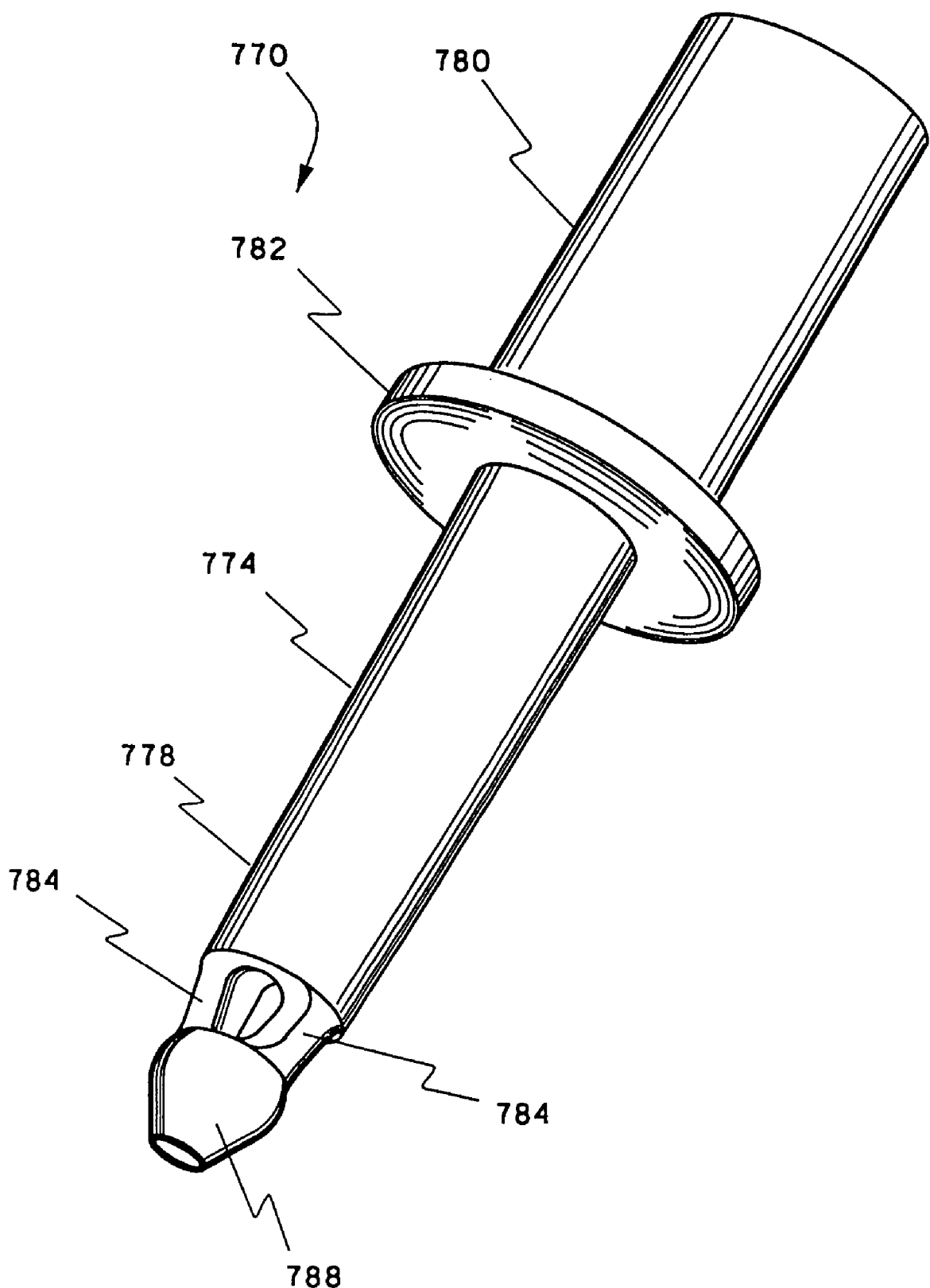
FIG. 14A shows a perspective view of an alternate embodiment of an occluder made in accordance with the principles of the present invention.
Figure 14B:
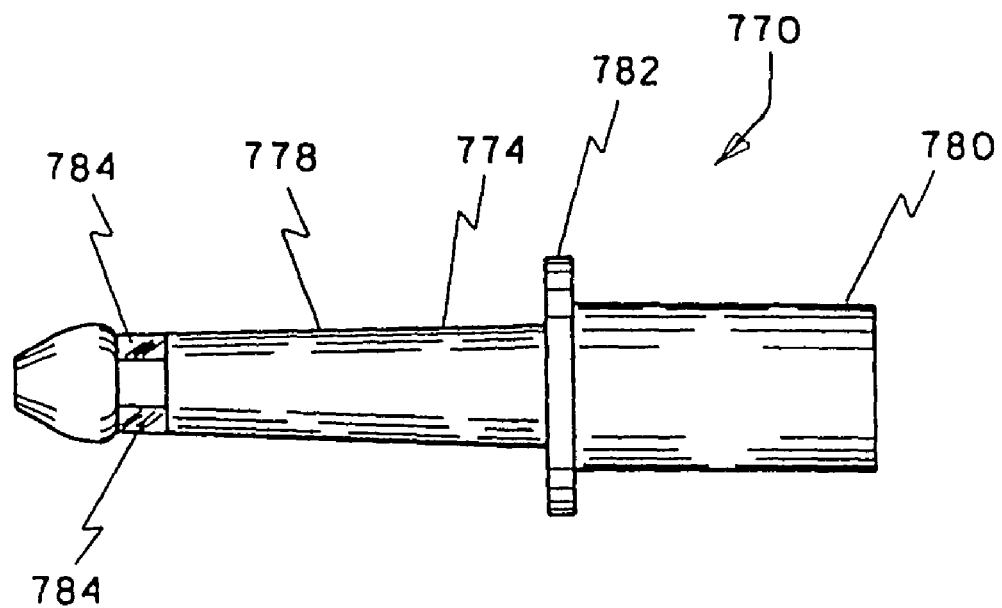
FIG. 14B shows a side view of the occluder of FIG. 14.
Figure 14C:
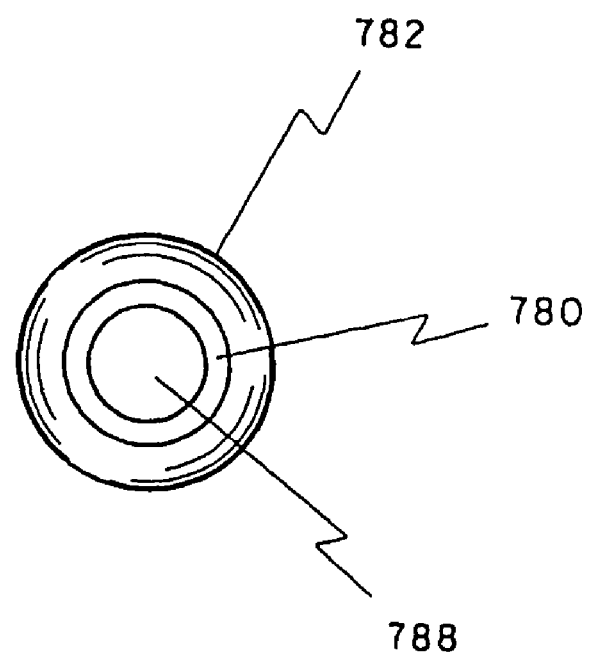
FIG. 14C an end view of the occluder of FIG. 14.

Turning now to FIGS. 14A to 14C, there is shown an alternate embodiment of a connector or adaptor, generally indicated at 770, made in accordance with the principles of the present invention. The connector 770 is typically formed by an adaptor body 774 which is used to connect two pieces of tubing together. However, it will be appreciated in light of the present disclosure that such a structure is not required. Most commonly, the adaptor body 774 is used to connect a silicone tube segment which engages the pump rotor, to the remaining tubing of an infusion set (not shown.)

The adaptor body 774 is formed by a proximal section 778, a distal section 780, and an annular flange 782 which limits the advancement of tubing along the proximal and/or distal sections of the adaptor body. The proximal section 778 usually engages the silicone tubing, while the distal section 780 engages the remaining tubing of the infusion set.

Rather than being connected by a tether/spacer as shown in FIGS. 13A and 13B which extends into the interior of the proximal section 778, the tether/spacer 784 forms a pair of arms which connect the occluder or stop 788 to the adaptor body 774. It has been found that using a pair of arms as the tether/spacer 784 decreases the risk of an obstruction preventing flow through the adaptor body 774. Because the arms 784 are not disposed in alignment with a hollow channel 790 in the adaptor body, greater unobstructed area is available for moving enteral feeding solution through the adaptor. This is especially true if the feeding solution is somewhat viscous. The arms forming the tether/spacer 784 are also advantageous in that they securely hold the occluder or stop away from the adaptor body 774 in a generally rigid manner and reduce the risk that the stop or occluder 788 will be broken off from the adaptor body.

By matching the occluder 788 with an appropriately sized infusion set tube, a valve can be formed which will open the valve to the flow of liquid once a predetermined pressure threshold has been reached, but generally prevent free flow when the pressure falls below the predetermined threshold. Those skilled in the art will appreciate that the pressure threshold at which the seal between the tubing and the occluder 788 will crack is a function of the relative sizes of both, along with the elasticity of the tubing.

Figure 15:
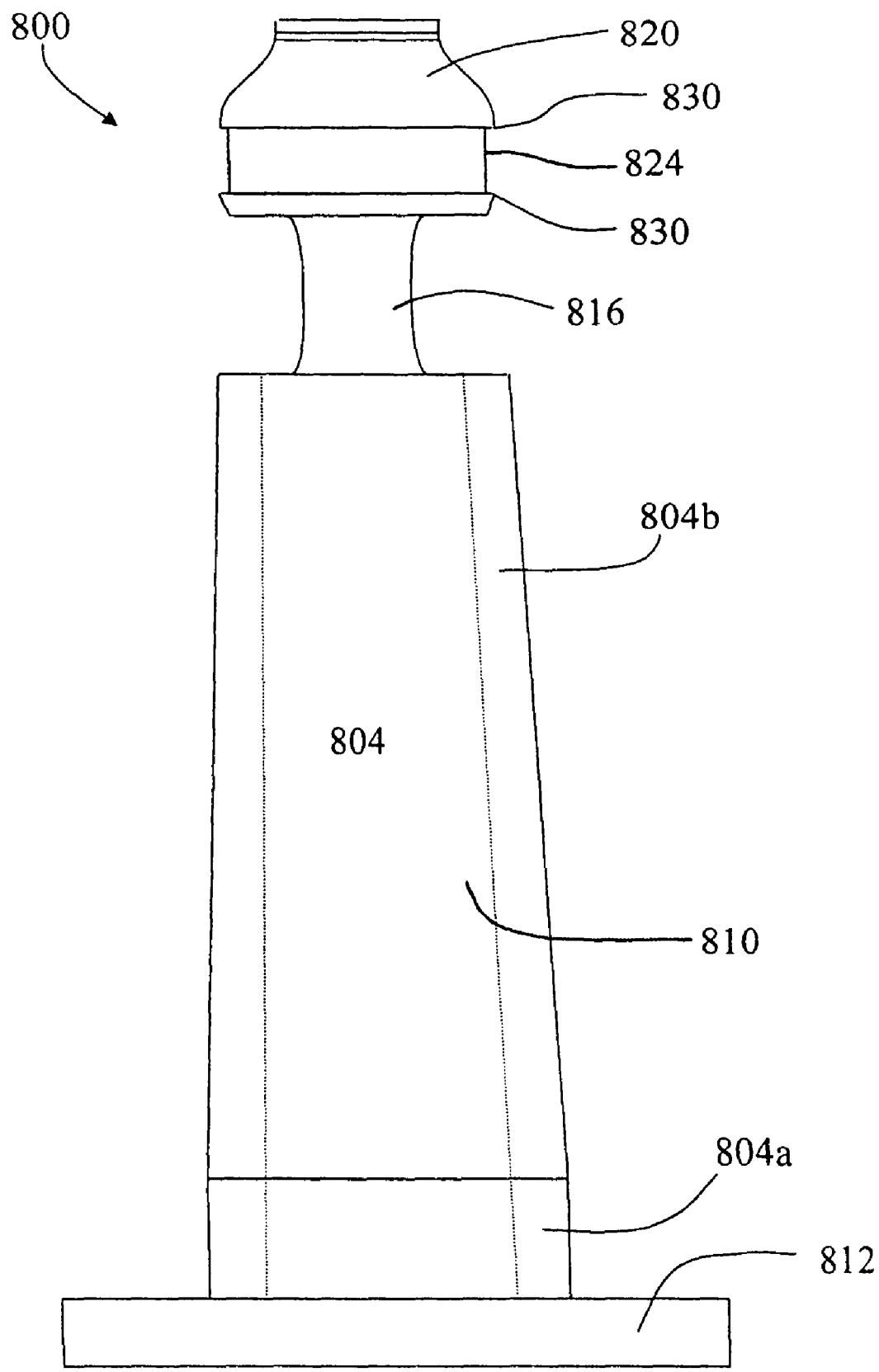
FIG. 15 shows a top view of yet another embodiment of an occluder made in accordance with the principles of the present invention.
Figure 15A:
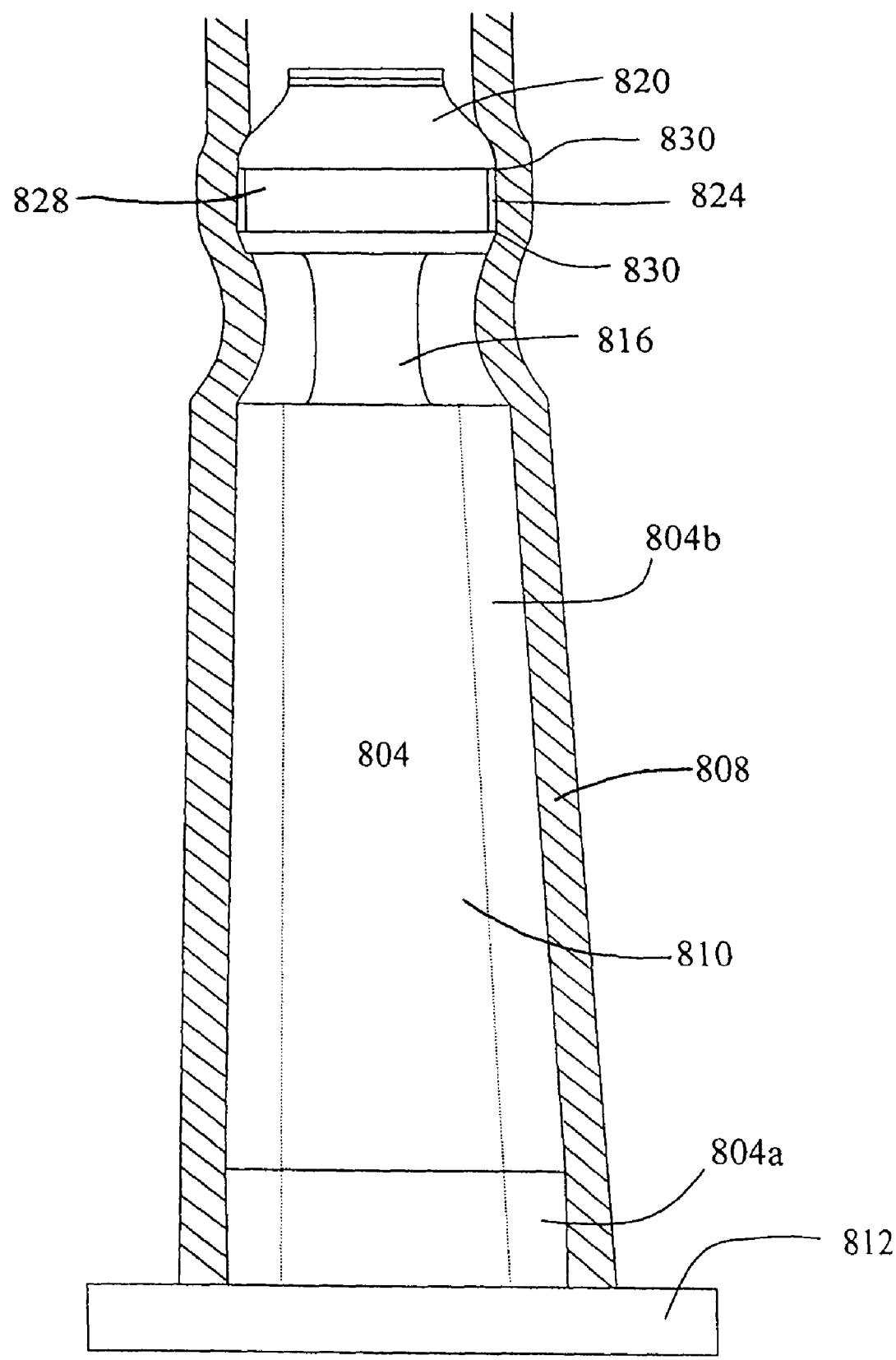
FIG. 15A shows a cross-sectional view of a portion of an infusion set with the occluder of FIG. 15 disposed therein.

FIG. 15 shows a top view of yet another embodiment of an in-line occluder, generally indicated at 800, made in accordance with the principles of the present invention. FIG. 15A shows the occluder 800 disposed in a tube 808 of an infusion set. The configuration is referred to generally as an in-line occluder simply to illustrate that the configurations shown herein can be used in conjunction with two tubes as an adaptor, or can be inserted into a single tube. It is presently preferred that the in-line occluder be used as an adaptor for connecting tubing segments. However, it should be appreciated that such is not a requirement and the in-line occluder 800 can be disposed completely within a single tube.

The in-line occluder 800 includes a body 804 configured to nest in a tube of an infusion set. To this end, the body 804 may include a generally cylindrical distal portion 804a and a tapered proximal portion 804b. The tapered portion 804b assists in the insertion of the body into the tube.

Attached to the distal portion 804a is a flange 812 which can be used for securing the position of the occluder 800 in an enteral feeding pump. If the body 804 were desired to be disposed completely in a tube, the flange 812 could be omitted.

Attached to the proximal portion 804a by one or more arms 816 is an occluder or stop 820. As with the previous embodiment, it is preferred to have two arms which connect the proximal portion or stop without extending into a hollow portion (not shown) of the body to thereby minimize interference with fluid flow.

One concern which has been raised with having a broadly rounded portion of the occluder or stop 820 which engages the tubing of an infusion set is that the friction between the stop 820 and the tubing can prevent the tubing from resealing against the stop after it has been activated to form a flow channel around the stop. If a seal is not maintained, a free flow condition could result, although it would typically have a very low flow rate.

In accordance with one aspect of the present invention, it has been found that an improved seal can be achieved by not using broadly rounded stops. More specifically, it has been found that providing the stop 820 with an annular detent or channel 824 in a sealing portion 828 provides an improved seal and virtually eliminates the risk of leakage. Furthermore, it may be preferred that the channel 824 is defined by relatively sharp edges 830. Thus, for example, the edges can have a radius of about 0.003 inches, plus or minus 0.002. The sloped walls at the proximal portion of the stop 820 are preferably disposed at an angle between about 60 and 70 degrees, and the back of the stop is preferably beveled at about 120 degrees. With the overall width being about 0.155 inches, the stop 820 forms a highly effective occluder in an infusion set tube.

Ironically, the relatively sharp edges and the channel 824 improve sealing by decreasing the amount of surface area over which the tubing and the stop 820 engage each other. The reduction in surface area minimizes the amount of friction for the tubing 808 to move from an open position back into a closed position once it is no longer being pinched or once the pressure in the tubing drops below the predetermined threshold. Effectively, the channel 824 allows the tubing to collapse more and to thereby form a better seal.

The channel 824 need not be large. To the contrary, a channel which is $30\text{-}40/1000$ths of an inch deep and $30/1000$ths to about $500/1000$ths wide works significantly better than a prior art configuration with a broadly rounded stop. More particularly, a channel which is between about $30/1000$ths to about $100/1000$ths of an inch wide works well in forming an effective seal between the occluder and the tubing. Of course, the remainder of the stop 820 can be any desired shape. Thus, as shown in FIGS. 15 and 15A, the stop 820 has a blunted proximal end.

It will be appreciated from FIG. 15A that the tubing 808 is able to form an effective seal around the occluder 820 by engaging the edges 830. The occluder 820 thus prevents flow around the occluder and through the tubing.

Figure 15B:
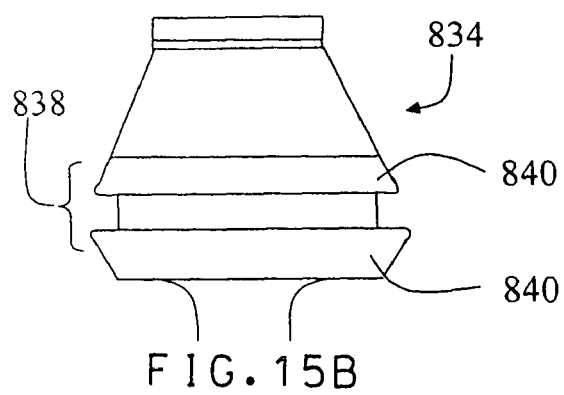
FIG. 15B shows a top view of a stop of an occluder showing an alternate configuration for the stop relative to that shown in FIG. 15.

Turning now to FIG. 15B, there is shown an alternate embodiment of an occluder or stop 834. The stop 834 will typically be attached to a body, which will not be discussed here. The stop includes a sealing portion 838 which is configured to seal against the tubing of an infusion set, etc. The sealing portion 838 in FIG. 15B is different than that shown in FIGS. 15 and 15A in that it provides a pair of bevels 840 in the sealing portion 838 of the stop. The bevels 840 help to form seals with an infusion tube by reducing friction and minimizing engaged surface area.

Figure 15C:
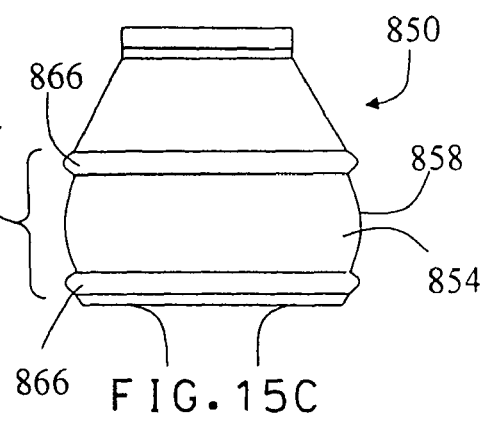
FIG. 15C shows a top view of an alternate embodiment of an occluder stop.

FIG. 15C shows an alternate embodiment of an occluder, generally indicated at 850, made in accordance with the principles of the present invention. The occluder 850 includes a stop 854. The stop 854 includes broadly rounded sides 858 disposed along the sealing portion 862. To facilitate sealing between the stop 854 and the tubing, one or more ribs 866 are disposed on the stop 854. The ribs 866 extend outwardly so that engagement of the ribs and the tubing of the infusion set encourages the tubing to flatten out in the sealing area 862 and form a seal with the ribs. Again, the reduced surface area of the ribs 866 which is engaged by the tubing helps to minimize friction and allow the tubing to quickly reseal in the event that it is not being pinched open or forced open due to the pressure in the tubing.

Figure 15D:
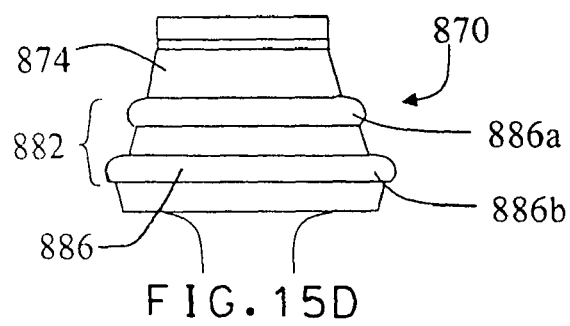
FIG. 15D shows a top view of another embodiment of an occluder stop.

Turning now to FIG. 15D, there is shown a fragmented view of an occluder, generally indicated at 870, which forms a stop 874. Disposed on the stop 874 in the sealing area 882 are a pair of annular ribs or rings 886. Unlike the ribs 866 shown in FIG. 15C, the ribs 886 of FIG. 15D do not extend radially outwardly to the same extent. Thus, a proximal rib 886*a* does not extend out as far as the distal rib 886*b*. Those skilled in the art will appreciate that with the ribs present, the underlying shape of the stop 870 becomes less important, as the ribs help form the seal with the tubing while minimizing friction.

Figure 15E:
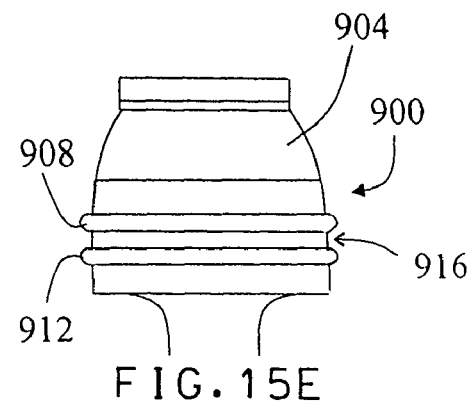
FIG. 15E shows a top view of yet another occluder stop made in accordance with the principles of the present invention.

FIG. 15E shows still another occluder, generally indicated at 900 which includes a stop 904 having a first rib or ring 908 and a second rib or ring 912 in the sealing area 916. While the ribs 908 and 912 extend generally radially to the same extent, they are different than the embodiment shown in FIG. 15C in that they are positioned close together. It will be appreciated in light of the present disclosure that the most desirable distance between ribs will be a function both of the curvature, if any of the exterior of the ribs, along with the relative elasticity, flexibility and friction of the tubing.

Figure 15F:
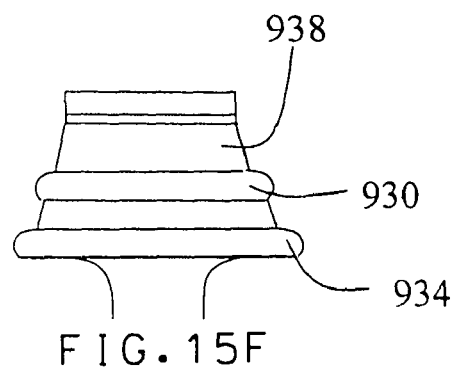
FIG. 15F shows a top view of still another stop of an occluder showing an alternate configuration for the stop relative to that shown in FIGS. 15 through 15E.

While the ribs 908 and 912 are relatively thin, broader ribs, such as ribs 930 and 934 on the stop 938 can be used as is shown in FIG. 15F. Thus, it will be appreciated that numerous different stop formations can be used to more securely effectuate sealing of the tubing to prevent free flow.

Figure 15G:
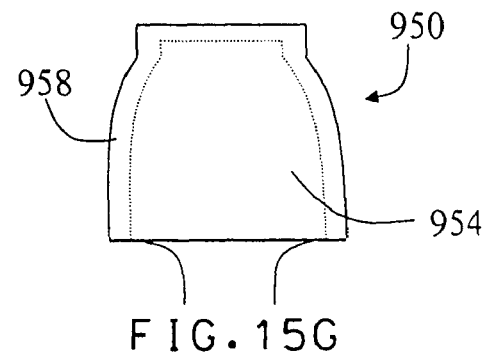
FIG. 15G shows a top view of still another stop of an occluder in accordance with the principles of the present invention.

FIG. 15G shows yet another embodiment of the stop, indicated at 950. The stop 950 includes an inner portion 954 which is shaped with a configuration generally similar to the shape shown in FIG. 13A. An outer layer 958 is disposed on the inner portion 954 to thereby increase its diameter. The outer layer may be formed with ABS and solvent, or in a variety of other ways known to those of skill in the art.

While shown in FIG. 15G as covering the entire inner portion, those skilled in the art will appreciate that the stop 950 could be dipped once or repeatedly into a ABS solution to provide a variety of different shapes. Thus, for example, the inner layer could be covered half way to thereby form a sealing rib about the inner portion at a desired location. The stop 950 could be dipped repeatedly to form multiple sealing ribs, etc.

Figure 15H:
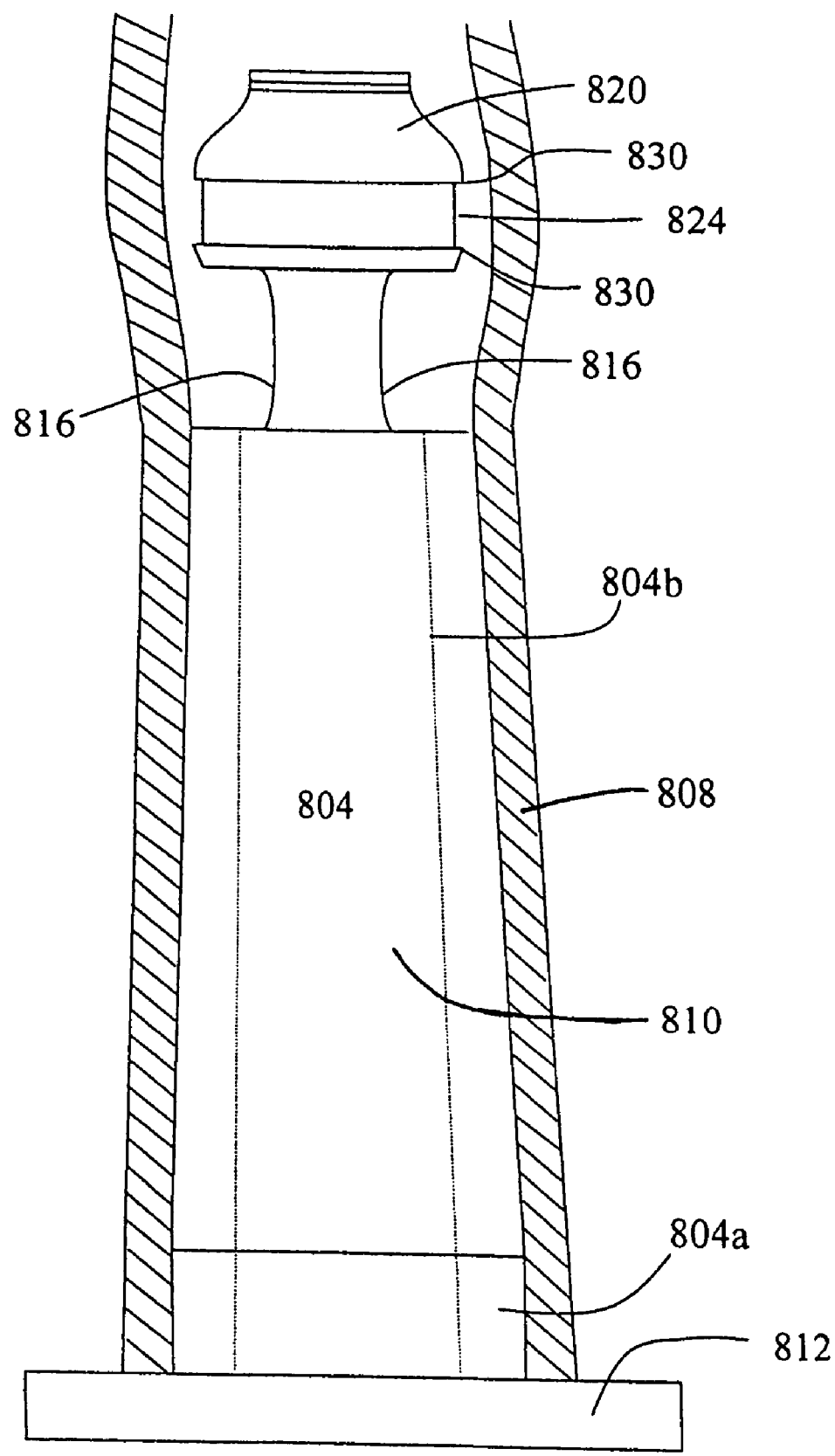
FIG. 15H shows a cross-sectional view of a portion of an infusion set with the occluder of FIG. 15 disposed therein.

FIG. 15H shows a fragmented cross-sectional view of an infusion set having an occluder disposed therein. The occluder and infusion set are similar to those of FIG. 15 and FIG. 15A and have accordingly been labeled with corresponding reference numerals. The tubing 808 adjacent the occluder 820 is expanded so as to form a gap between the inside bore of the tubing and the occluder. This may commonly occur during use when a pump generates sufficient pressure to force fluid past the occluder 820. After flowing past the occluder 820, the fluid is typically delivered to a patient. It will be appreciated that the tubing 808 may be expanded as shown with every pumping stroke and collapse back to the position shown in FIG. 15A between every pumping stroke. Thus, it is important to have a type of tubing 808 and an occluder 820 design which allow for consistent sealing between the tubing and the occluder.

Figure 16:
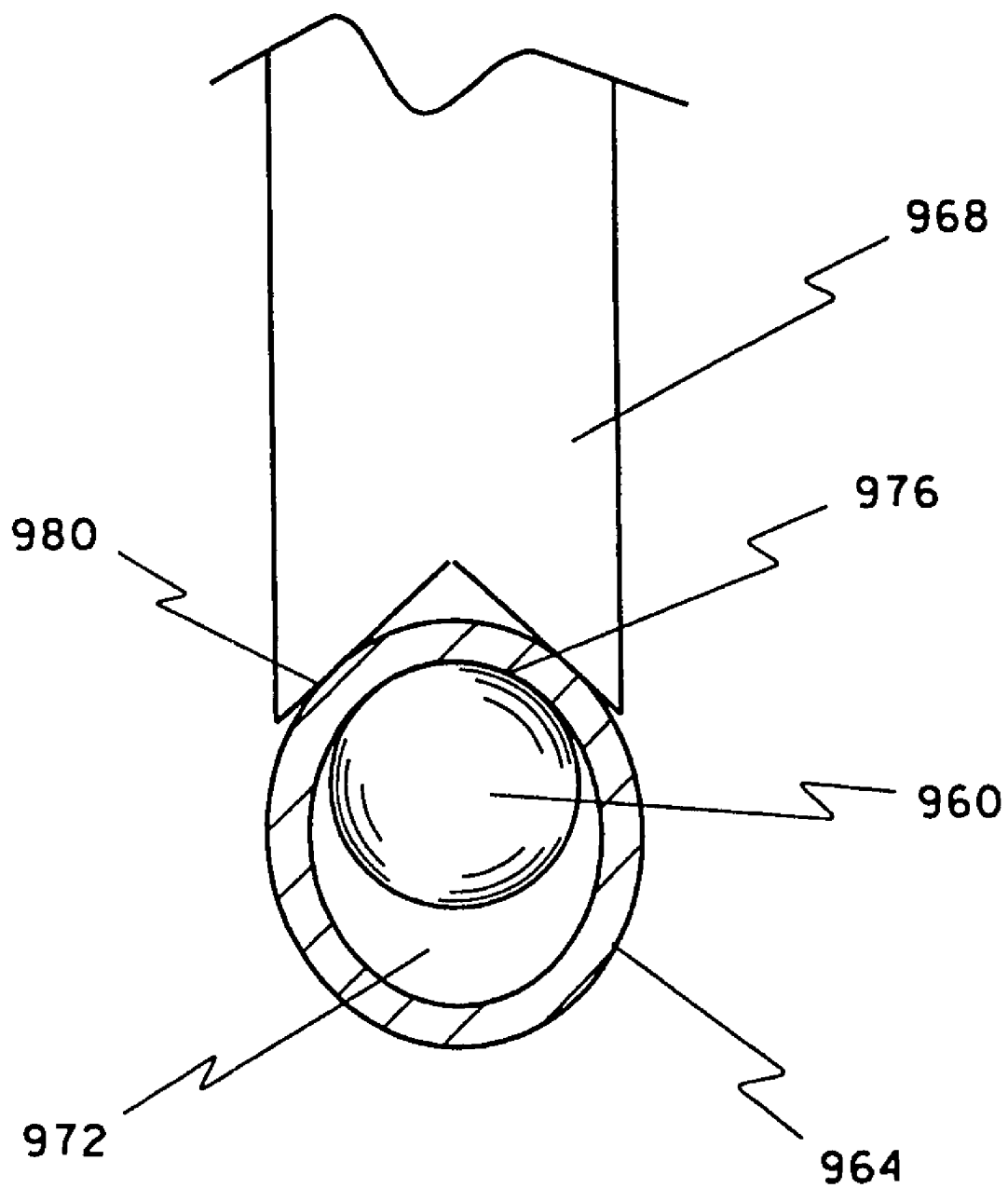
FIG. 16 shows a fragmented, cross-sectional view of an infusion set tube with an occluder disposed therein and a control mechanism to maintain the infusion set and occluder in an open configuration.

Turning now to FIG. 16 there is shown a cross-sectional view of an infusion set with an occluder disposed therein. While FIGS. 5C-D and 9-11 above discuss embodiments wherein flow through the infusion set is enabled by compressing opposing sides of the tube against the occluder, it has been found in accordance with the present invention that a preferred configuration involves compressing the tube from generally one side to open a single fluid passage between the occluder and the tubing. Thus, as shown in FIG. 16, an occluder 960 is disposed in a tube 964. An actuator 968 is disposed to forcefully engage the tube 964 to open a fluid flow path 972 past the occluder.

The actuator 968 is configured to press on one side of the occluder, but not on both sides as discussed in the previous embodiments. The actuator 968 preferably has two engagement surfaces 976 and 980. The two engagement surfaces 976 and 980 are preferably spaced apart at an angle of less than 150 degrees, more preferably between about 90 and 135 degrees, and ideally about 110 degrees.

Because the engagement surfaces 976 and 980 of the actuator are offset but not opposite one another, they have a tendency to force the tubing in such a way that a single fluid flow channel 972 is formed passed the occluder 960. A single fluid flow channel 972 provides for more area and is less likely to be occluded by a viscous solution or a fibrous solution. When combined with the occluder configurations of FIGS. 14 and 15, the risk that the occluder will increase the likelihood of an unintended occlusion is significantly reduced. Furthermore, only requiring the movement of a single actuator decreases the complexity and cost of an enteral feeding pump.

Figure 17:
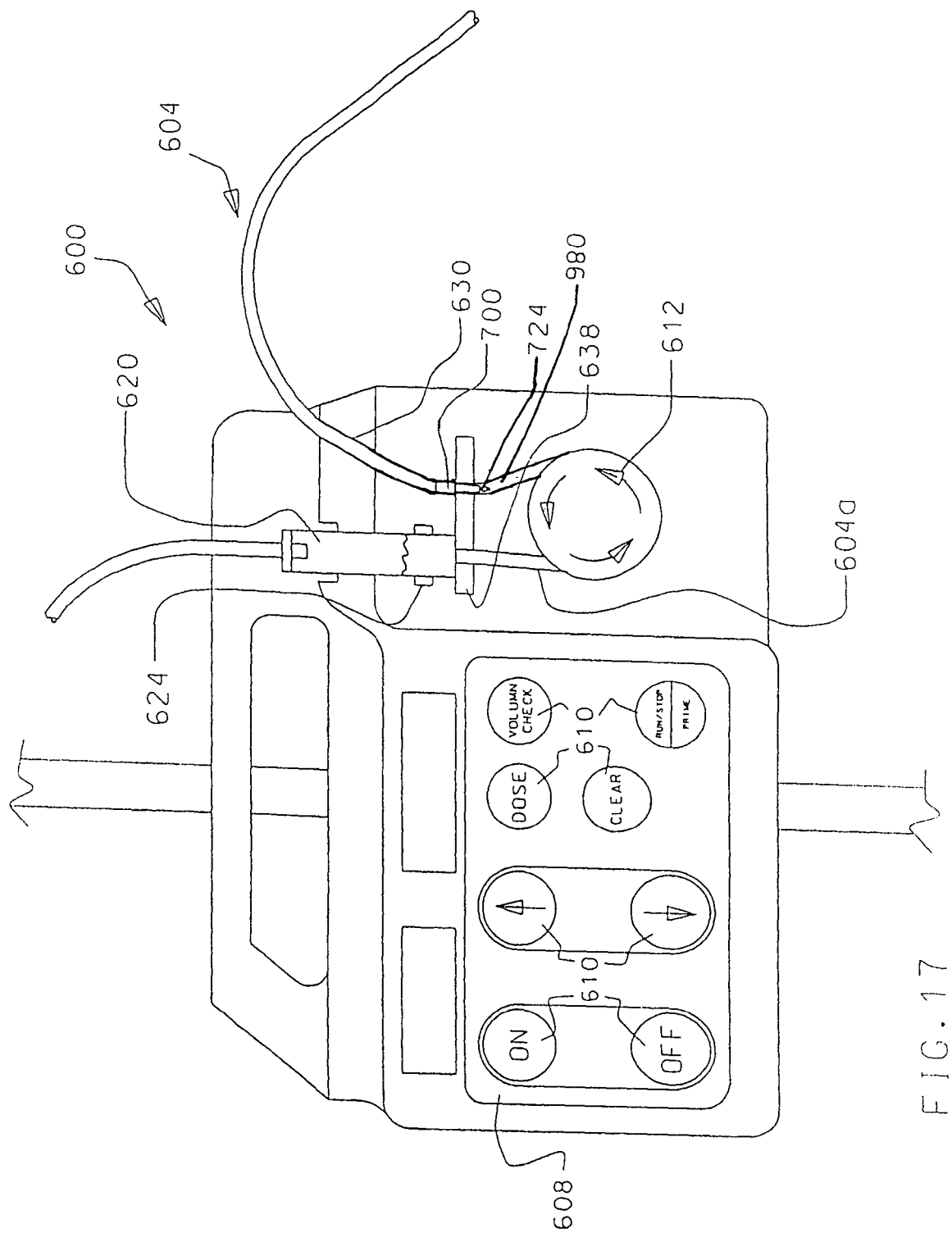
FIG. 17 shows a front view of an enteral feeding pump having an infusion set disposed therein.

Turning now to FIG. 17, a front view of a pump is shown. The pump, indicated generally at 600, is similar to the pumps shown in FIG. 12A and FIG. 13E. The bracket 638 has been formed such that the connector 700, and thus occluder 724 have been mounted further left, towards the center of the rotor 612 as compared to the pump 600 of FIG. 13E. The connector 700 and occluder 724, however are held substantially perpendicular to the bracket 638 and are not in linear alignment with the tubing 980 leading to the pump rotor 612. Mounting the connector 700 and occluder 724 further to the left as shown causes the connector and occluder to be held at an angle relative to the tubing 980. This creates an area of increased pressure between the occluder 724 and tubing 980 on one side of the occluder, and an area of reduced pressure between the occluder and tubing on the opposite side of the occluder, making it easier for the pump rotor 612 to push liquid past the occluder.

It will be appreciated that the degree to which the occluder 724 is pulled off axis relative to the tubing 980 determines the degree to which an area of reduced sealing pressure is formed between the occluder and tubing. Thus, the occluder 724 may be oriented such that the sealing pressure between the occluder and tubing 980 is slightly reduced, such that the seal is almost broken and easily overcome by the rotor 612, or such that the seal is broken and a channel is formed between the occluder and tubing. Once the infusion set 604, 604a, 980 is properly mounted in the pump 600, the rotor 612 prevents free flow in the infusion set and the occluder 724 may be bypassed by opening a flow channel between the occluder and tubing. Thus, a pump 600 and infusion set 604 may be designed such that free flow is prevented in the infusion set by the occluder, such that the pump rotor 612 prevents flow through the infusion set once the infusion set is properly loaded, and such that a flow channel around the occluder 724 is formed once the infusion set is properly loaded.

It will be appreciated that many different occluder designs may be used in such a configuration. That is to say that many different occluder designs and stop designs, including ribbed and non-ribbed occluders, may be mounted into a pump so as to maintain the occluder at an angle relative to the tubing and thereby alter the sealing characteristics of the occluder. The occluder may be similar to those shown in FIG. 13A-13C, 14A-14C, 15-15H, or 18-25.

Figure 18:
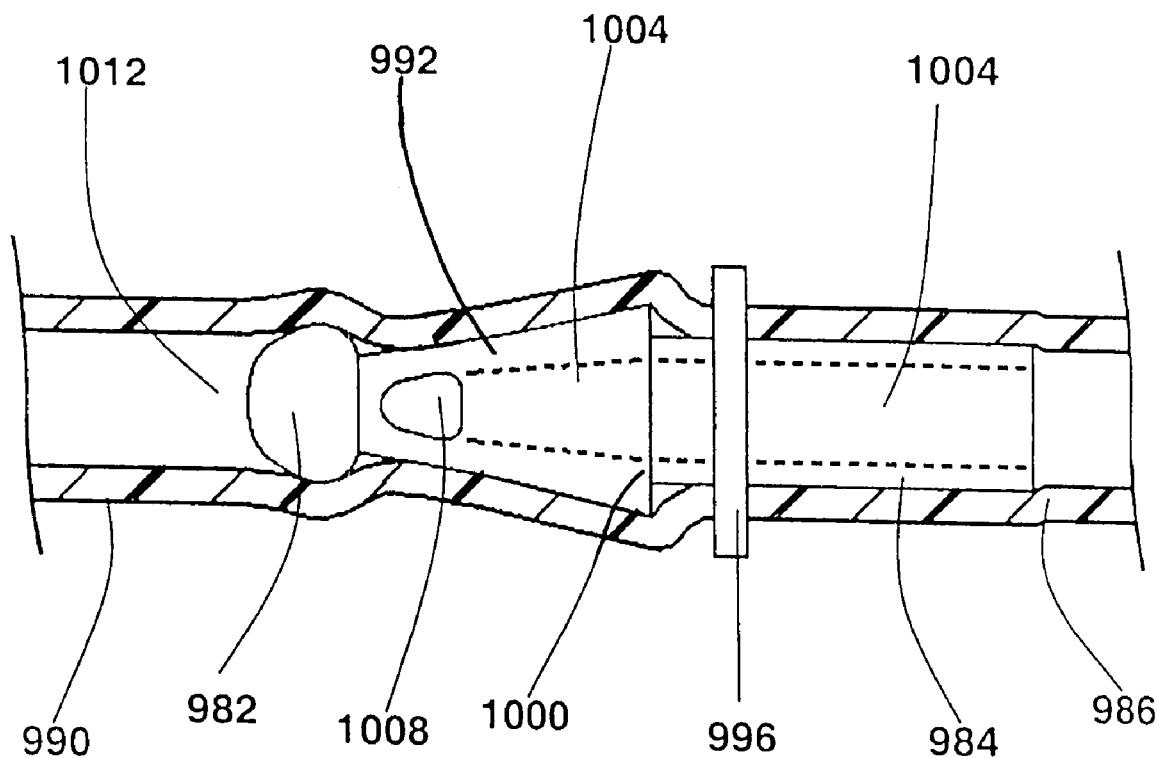
FIG. 18 shows a fragmented cross-sectional view of an infusion set tube and occluder according to the present invention.

Turning now to FIG. 18, a side view of an occluder according to the present invention and a cross-sectional view of infusion set tubing is shown. The occluder 982 is generally similar to the occluder shown in connection with pump 600 of FIG. 17. The occluder 982 is attached to connector 984 by a stem or body 992. A flange 996 may be formed between the connector 984 and stem or body 992. The flange 996 may help locate the tubing 986, 990 or may help secure the occluder 982, connector 984, etc. in the pump housing. The stem or body 992 may be formed with a shoulder 1000 to help secure tubing 990 and prevent the rotor 612 (FIG. 17) from moving the tubing 990. The shoulder 1000 may be formed as angular ridge, or may be rounded as is desired. A conduit 1004 is formed through connector 984 and stem or body 992 which extends through the end of the connector 984 and which is connected to at least one opening 1008 such that the bore of tubing 986 is connected to the bore of tubing 990 between the occluder 982 and stem or body 992. The stem or body 992 may be formed with multiple openings 1008 so as to form arms attached to the occluder 982. Tubing 990 is typically a flexible tubing, such as silicone tubing, as is necessary for proper operation of the pump 600 (FIG. 17).

In operation, pressurized liquid from the pump 600 (FIG. 17) in area 1012 adjacent occluder 982 may cause the tubing 990 adjacent the occluder 982 to expand, forming a flow channel around the occluder 982. Fluid then flows through opening 1008, through conduit 1004, and into tubing 986.

Figure 19:
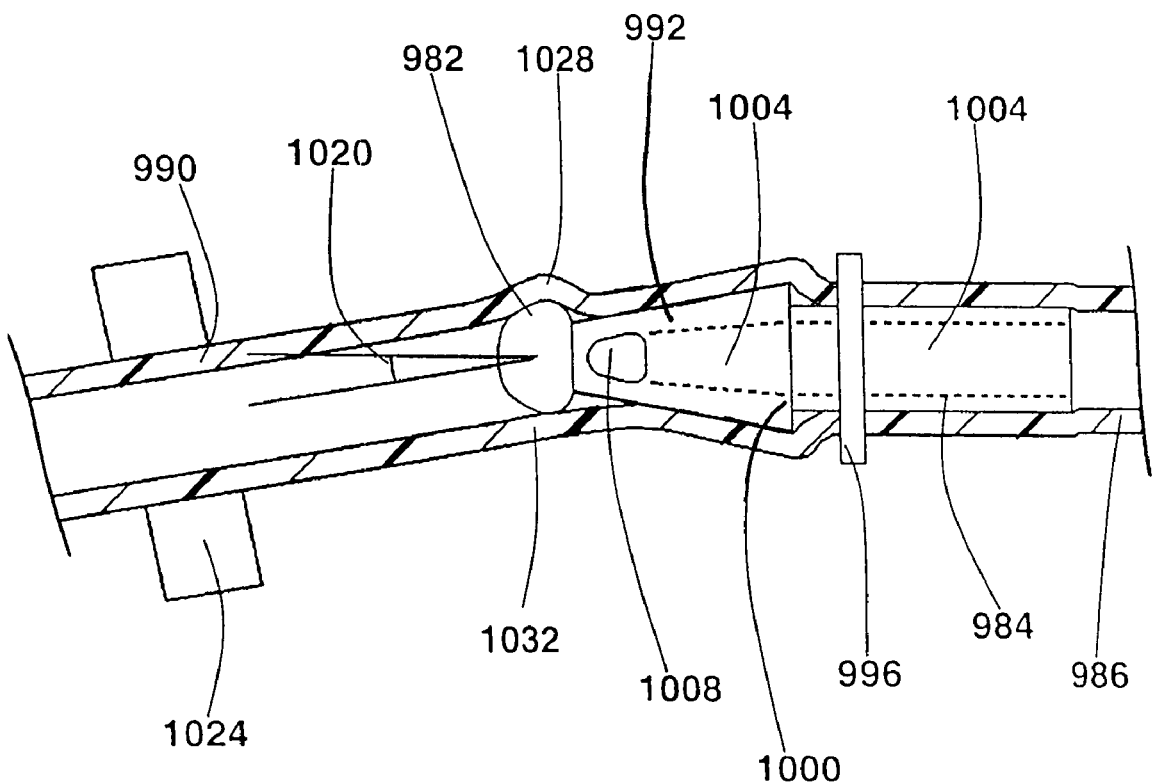
FIG. 19 shows a fragmented cross-sectional view of an infusion set tube and occluder according to the present invention.

Turning now to FIG. 19, a side view of another occluder according to the present invention is shown. The occluder 982 is similar to that of FIG. 18, and similar reference numerals are used. In FIG. 19, the tubing 990 which is disposed between the occluder 982 and the pump rotor 612 (FIG. 17) is held at an angle 1020 relative to the occluder 982 and stem or body 992. The tubing 990 may be held at angle 1020 by the position of the occluder 982 and connector 984 relative to the pump rotor 612 as is shown in FIG. 17. Alternatively, a bracket 1024 may be used to hold the tubing 990 at angle 1020. The bracket 1024 may simply be a projection disposed on the pump 600 (FIG. 17) such that once the infusion set is properly loaded into the pump 600, the projection 1024 pushes the tubing so as to alter the sealing ability of the occluder 982. Thus, bracket 1024 may be a lever or bracket which is moved into place after loading the infusion set, or the bracket 1024 may be formed as part of a pump door which is closed after loading the infusion set. Holding the tubing 990 at angle 1020 creates a greater pressure between tubing 990 and occluder 982 at area 1028 and lower pressure between the tubing 990 and occluder 982 at area 1032, making it easier for the pump 600 (FIG. 17) to break the seal at area 1032. (While shown with the occluder 982 and connector 984, it will be appreciated that any occluder configuration consistent with those discussed herein or modifications thereof could be used.)

Figure 20:
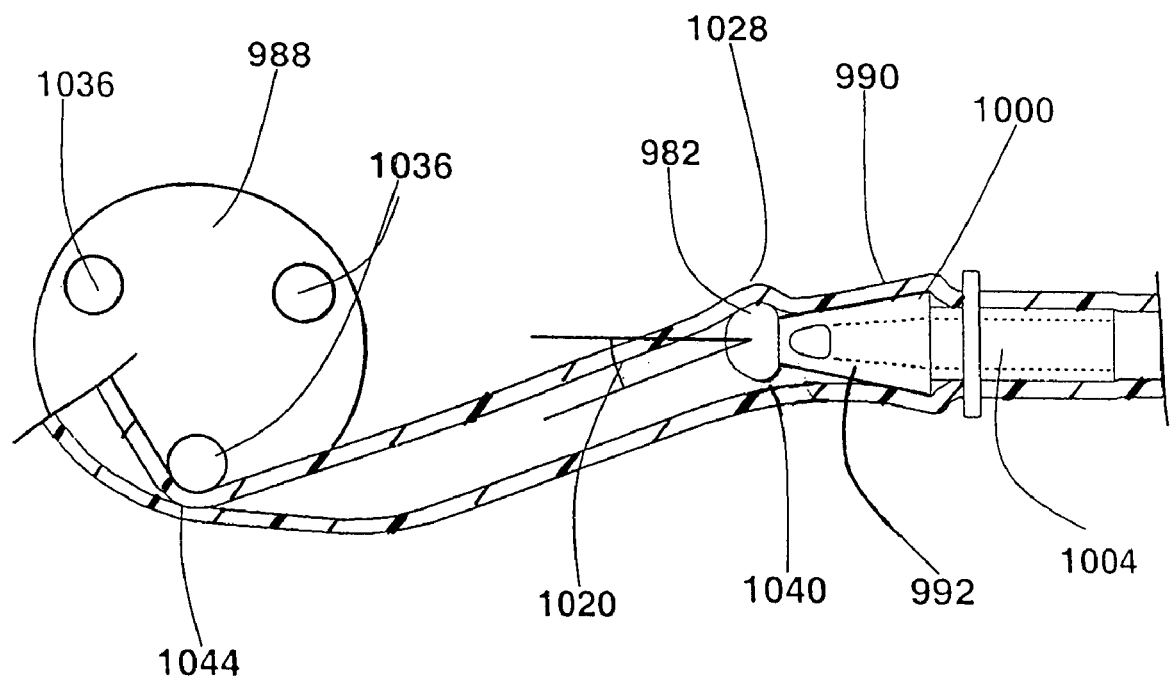
FIG. 20 shows a top fragmented cross-sectional view of an infusion set tube, occluder, and pump rotor according to the present invention with the infusion set engaging the roller of a peristaltic pump.

Turning now to FIG. 20, a side view of another occluder according to aspects of the present invention is shown. An occluder 982 and stem or body 992 similar to those of FIG. 19 are shown. The occluder 982 has been mounted such that the angle 1020 between the occluder 982 and stem or body 992 and the tubing 990 is increased. This has been accomplished by selecting a mounting location for the occluder 982 relative to the pump rotor 988 and rollers 1036 so as to form the desired angle 1020. The occluder 982 has been oriented so as to form an angle 1020 sufficient to form a gap 1040 adjacent occluder 982. According to one embodiment of the invention, the mounting location of the occluder is selected such that a maximum angle 1020 of approximately 25 degrees between the axis of the occluder stem or body 992 and the axis of the tubing 990 is obtained during the rotation of the pump rotor 988. It is preferable that angle 1020 is between 10 and 60 degrees and more preferable that the angle is between 10 and 40 degrees, and even more preferably about 25 degrees.

Once the feeding set is properly placed in the pump 600 (FIG. 17), the tubing is pinched closed adjacent the rollers 1036 of the rotor 988, such as at area 1044. Thus, it is not necessary that the occluder 982 continue to prevent flow after properly loading the infusion set into the pump, and a flow channel or gap 1040 may be formed adjacent the occluder 982. It will be appreciated that the distance between the occluder 982 and the pump rotor 988, and the orientation of the occluder 982 relative to the pump rotor 988 determine the angle 1020 formed between the occluder 982 and tubing 990. Thus, the design of the pump, including the placement and orientation of the occluder 982, may be adjusted to provide the desired amount of sealing pressure adjacent the occluder 982 or the gap 1040 formed adjacent the occluder 982 once the infusion set is loaded into the pump.

Figure 21:
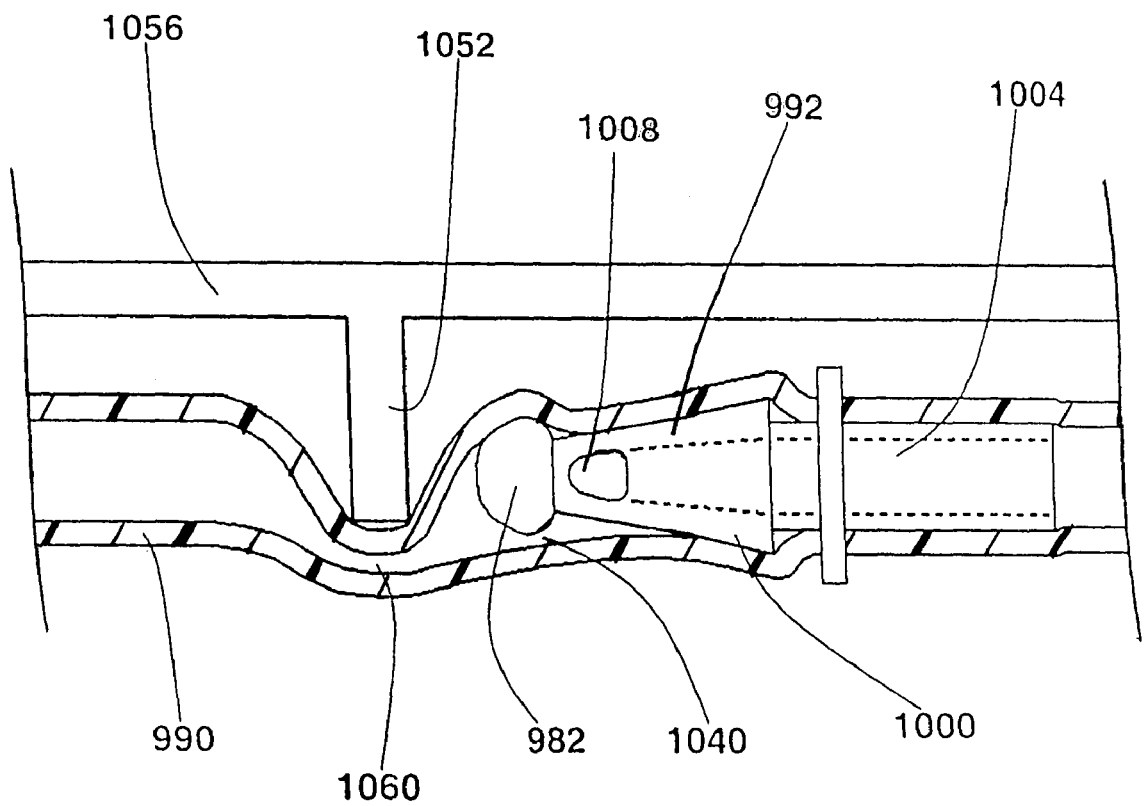

Turning now to FIG. 21, a side view of another occluder according to the present invention is shown. The occluder 982 is similar to that of FIG. 18 and FIG. 19 and is numbered accordingly. A projection 1052 is used to apply force to the tubing 990 adjacent the occluder 982, so as to push the tubing 990 down or sideways and deform the tubing 990. The projection 1052 may be configured such that the projection is moved into place after the infusion set, including tubing 990 and occluder 982, is mounted into the pump 600 (FIG. 17). Accordingly, the projection 1052 may be mounted to a lever or arm 1056 which is moved into place after mounting the infusion set. The arm 1056 may secure the tubing 990 and aid in keeping the infusion set properly loaded in the pump 600 (FIG. 17). The lever or arm 1056 may be all of or a part of a pump door.

The arm 1056 and projection 1052 may be configured to displace the tubing 990 by varying distances as is desired. Moving the tubing 990 a small distance will reduce the pressure required from the pump 600 (FIG. 17) to create flow around the occluder 982. Moving the tubing 990 a greater distance may open a gap or flow channel 1040 adjacent the occluder 982, as is shown in FIG. 21. It will be appreciated that it is typically undesirable to move the tubing such a distance that the bore 1060 of the tubing 990 is closed adjacent the projection 1052, preventing flow through the tubing.

Various parameters of the occluder and projection assembly shown may be adjusted to adjust the flow and sealing characteristics of the occluder. The diameter of the occluder 982 may be adjusted relative to the bore of the tubing 990. Increasing the diameter of the occluder 982 would increase the cracking pressure and decrease the size of the gap 1040, and vice-versa increasing the length of the projection 1052 and the distance between the projection 1052 and the occluder 982 will alter how far the tubing 990 is displaced and how much of a gap 1040 is formed. According to one embodiment of the invention, the diameter of the occluder 982 is approximately 0.13 inch and is slightly larger than the bore of the tubing 990. The projection 1052 is approximately 0.07 inch wide and is disposed at a distance of approximately 0.08 inch from the tip of the occluder 982, and has a length such that the projection displaces the tubing by a distance of about 0.18 inch.

Figure 22:
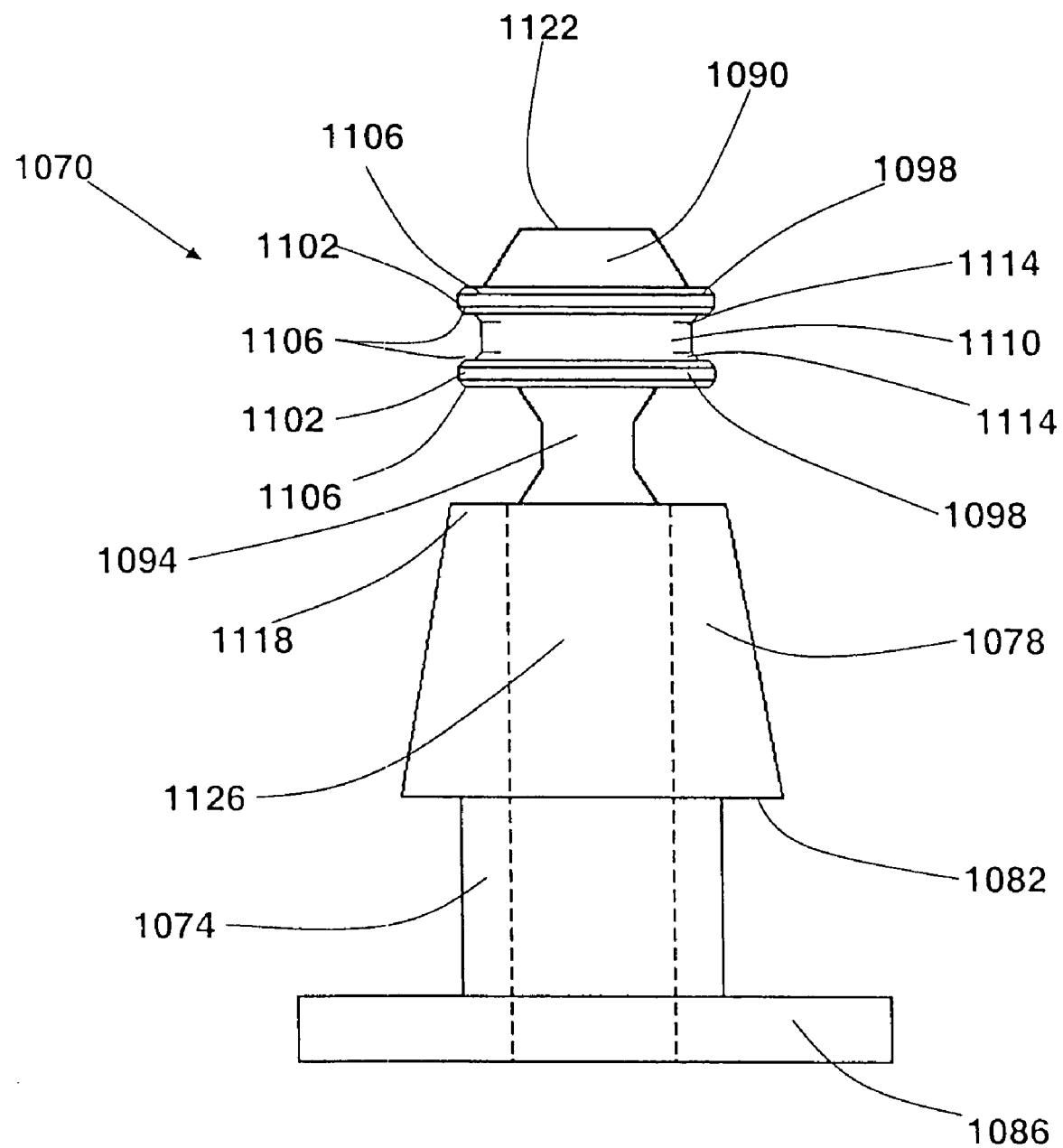
FIG. 22 shows a side view of an alternate embodiment of an occluder according to the present invention.

Turning now to FIG. 22, a side view of an occluder according to the present invention is shown. The occluder, generally indicated at 1070, is shown with a distal body portion 1074 which is cylindrical and which is attached to a tapered proximal body portion or stem 1078 so as to form a shoulder 1082. Although not necessary, the presence of shoulder 1082 helps secure the infusion set tubing to the occluder body. A flange 1086 may be formed on the occluder and may be used to help locate the infusion set tubing or to help secure the occluder in a pump. The distal end of the occluder 1070, such as distal body portion 1074, may also be attached to a pump cartridge or a connector, or may be formed as an integral part of a connector, pump cartridge, or infusion cartridge.

An occluder 1090 is attached to the proximal body portion 1078 via arms 1094. Typically, a pair of arms 1094 are used, but a single arm may be used if properly formed. The arms 1094 are preferably disposed out of alignment with the center axis of the occluder, such that the arms 1094 do not interfere with the flow of liquid through a center bore 1126 formed in the occluder 1070, although a central arm can be used. The occluder 1090 is designed to engage the infusion set tubing (as shown in FIG. 15A) and prevent undesired flow through the tubing. Applicant has found that the occluder 1090 works better if one or more ribs 1098 are formed on the occluder 1090. The ribs 1098 are shown having a generally cylindrical outer surface 1102 with chamfered or rounded edges 1106. Two ribs 1098 are shown according to a presently preferred embodiment, but a single rib 1098 may also be used. A channel 1110 is formed between the ribs 1098. A slight bevel 1114 may be formed between the channel 1110 and the ribs 1098. As has been previously discussed, the ribs need not protrude excessively from the occluder 1090. The ribs 1098 may protrude between about 0.005 and 0.05 inches, and more preferably about 0.02 inch. The channel 1110 between the ribs 1098 may be between about 0.02 and 0.06 inches, and more preferably about 0.04 inches.

The occluder 1090 has been formed such that the proximal end 1118 of the proximal body portion or stem 1078 is slightly greater in diameter than the ribs 1098. Forming the proximal end 1118 greater in diameter than the ribs 1098 aids in the formation of a flow channel adjacent the ribs 1098 when the infusion set tubing is pulled off axis as is shown in FIG. 20. The proximal end 1118 of the body portion 1078 may be between about 0.01 and 0.06 inches greater in diameter than the occluder 1090. The proximal portion 1122 of the occluder 1090 may be formed so as to taper to a smaller size as the proximal portion 1122 extends away from the ribs 1098, aiding in the formation of a flow channel around the occluder head when the infusion set tubing is pulled sideways. The proximal portion 1122 of the occluder 1090 should taper somewhat quickly so as to not interfere with the movement of the infusion set tubing as the tubing is pulled sideways. The proximal portion 1122 should taper at an angle of at least 10 degrees, and more preferably at an angle between 20 and 60 degrees. It has also proved advantageous to form the proximal end 1122 of the occluder 1090 as a flat surface. While not strictly necessary to the operation of the occluder 1070, forming the proximal end 1122 of the occluder 1090 as a flat surface facilitates manufacture of the occluder as plastic may be injected into the occluder mold via the proximal end of the occluder and then finished as a flat surface (1122), allowing for tighter tolerances in the occluder 1090 and relatively simple methods of molding the occluder.

Figure 23:
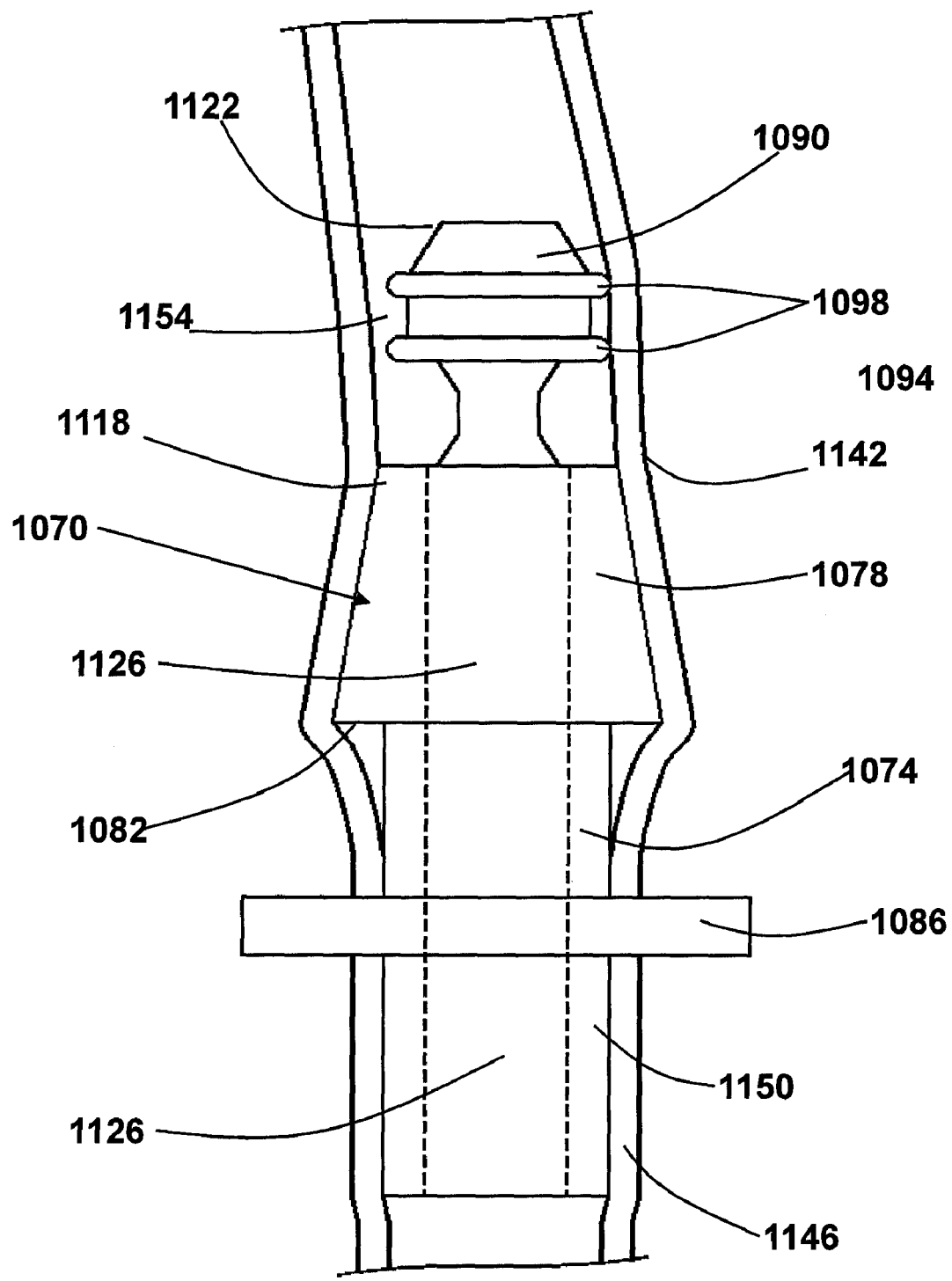
FIG. 23 shows a fragmented cross-sectional view of an infusion set tubing and still another embodiment of an occluder according to the present invention.

Turning now to FIG. 23, a side view of another occluder and cross-section of a portion of an infusion set according to the present invention are shown. The occluder 1070 is formed in a manner similar to the occluder 1070 of FIG. 22, and shares similar structures as is shown. A tapered proximal body portion 1078 is formed adjacent a distal body portion 1074 which is smaller in diameter than the adjacent part of the proximal body portion 1078 such that a shoulder 1082 is formed which helps to secure the pumping portion 1142 of the infusion set tubing. A flange 1086 is formed on the occluder 1070 to aid in locating the pumping section 1142 and distal portion 1146 of the infusion set. A connector 1150 is provided whereby the distal tubing 1146 may be attached to the occluder 1070.

A bore 1126 formed through the occluder 1070 allows the flow of fluid through the body of the occluder and through distal tubing 1146 after moving past the occluder 1090. The ribs 1098 formed on the occluder 1090 are formed as rounded ribs. Flow is allowed past the occluder 1090 if sufficient pressure exists in the fluid (typically generated by a pump) of if the tubing 1142 has been displaced sufficiently to open a flow channel 1154 past the occluder 1090 as is shown. The proximal end of the pumping tubing 1142 of the infusion set is shown disposed at an angle of about 20 degrees relative to the axis of the occluder 1070. The tubing 1142 may be held at such an angle relative to the occluder 1070 by controlling the orientation of the occluder in the pump, by using a projection such as on the pump door to displace the tubing, etc. The arms 1094 are disposed so as to not interfere with the flow of liquid out of the bore 1126 and past the occluder 1090.

It is important to control the gap 1154 between the tubing 1142 and the occluder ribs 1098 so as to optimize the flow past the occluder. A smaller gap 1154 will cause a higher fluid pressure drop across the occluder 1070. Conversely, a larger gap 1154 will cause a lower fluid pressure drop across the occluder 1070. Typically, a peristaltic pump will work more accurately with a smaller pressure drop across the occluder. Additionally, a typical peristaltic pump will generate about 10 psi of pressure. If the pressure drop across the occluder during fluid flow is higher than 10 psi, the pump will not be able to create flow. Additionally, the feeding solution which might be used in an enteral feeding pump and infusion set may be a mixture containing some food particles instead of being a completely liquid solution. If the gap 1154 is smaller than the diameter of any food particles, the particles will tend to clog the infusion line adjacent the occluder and may thus inhibit the flow of the feeding solution through the infusion set.

Various parameters of the occluder are adjusted to control the cracking pressure of the occluder and a particular infusion tubing 1142, the size of the gap 1054, etc. In designing an occluder, it is important to consider that the pressure generated by gravity in a vertically extended infusion set is about 3-4 psi, and that the pressure generated by a typical peristaltic pump is about 10 psi. Thus, the occluder must have a cracking pressure (the pressure at which flow will begin past the occluder) greater than 3-4 psi for an unloaded occluder, and a pressure drop of less than 10 psi across the occluder when feeding solution is flowing past the occluder.

The distance between the occluder 1090 and the proximal end 1118 of the proximal portion of the body 1078 and the difference between the diameter of the proximal portion 1118 and the diameter of the ribs 1098, in combination with the angle of the tubing 1142 relative to the center axis of the occluder 1070 and the tubing properties such as elasticity and size determine the size of the gap 1154. Shortening the distance between the occluder 1090 and the proximal end 1118 of the occluder body section 1078, and increasing the diameter of the proximal end 1118 help to increase the size of the gap 1154, but tend to decrease the cracking pressure. Increasing the angle of the tubing 1142 relative to the occluder axis helps to increase the size of the gap 1154. If the taper 1122 of the proximal portion of the occluder 1090 is too shallow, the end of the occluder 1090 may interfere with the tubing 1142 as the tubing is pulled sideways. Increasing the diameter of the ribs 1098 raises the cracking pressure, but lowers the size of the gap 1054. It will thus be appreciated that the various dimensions and properties of the occluder 1070 and the tubing 1142 may be adjusted to optimize the sealing and flow properties of the occluder/tubing combination.

The design of the occluder 1070 may be selected so as to facilitate mounting into an infusion pump. Thus, the occluder body 1078, 1074 may fit into a corresponding recess in the pump housing. Alternatively, the connector 1150 may fit into a recess formed in the pump housing, or both the body 1074, 1078 and connector 1150 may fit into a recess in the pump. The flange 1086 may be used to further secure the occluder 1070, and may fit into a slot or recess formed into the pump housing or may abut a corresponding flange or projection formed on the pump. The flange 1086 may thus inhibit movement of the occluder once loaded into the pump. In the configuration shown in FIG. 17, the pump 600 has a bracket 638 formed thereon and being configured for receiving an occluder 724, 1070 (FIG. 23). For such an arrangement, the body 1074, 1078 of the occluder 1070 would fit into a slot formed in the bracket 638 and the flange 1086 would abut the bracket 638, preventing movement of the occluder towards the pump rotor 612 and maintaining the proper tension in the tubing 980.

Figure 24:
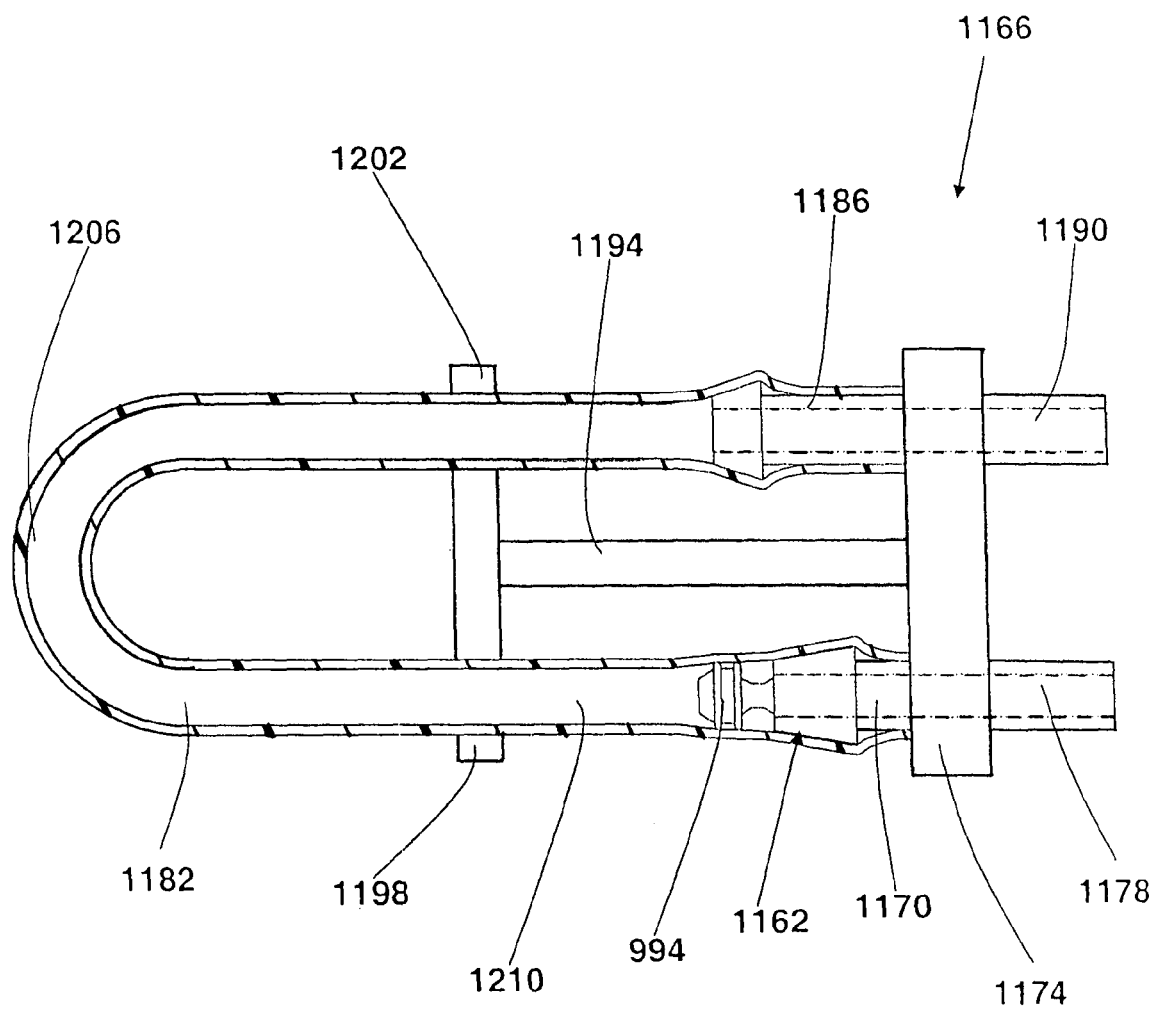
FIG. 24 shows a top view of a pump cartridge and occluder and cross-sectional view of an infusion set tubing according to the present invention.

Turning now to FIG. 24, a top view of an occluder and pump cartridge according to the present invention is shown. The occluder is indicated generally at 1162 and the connector is indicated generally at 1166. The occluder is formed as shown and described with respect to FIGS. 22 and 23 and includes the features thereof. The occluder body 1170 is attached to the body 1166 of a pump cartridge, and is in fluid communication with first connector 1178 which is used to attach the cartridge 1166 to a distal portion of an infusion set. A pumping section tubing 1182 of the infusion set is attached to the occluder and to a second connector 1186 which is in fluid communication with a third connector 1190, used to attach the cartridge 1166 to a proximal portion of the infusion set. An arm 1194 may be provided which supports the tubing 1182, such as at locations 1198, 1202. The arm 1194 may also be used to position and stabilize the cartridge 1166 within a pump.

As shown, the cartridge 1166 has many advantages. The cartridge 1166 may be provided with the various sections of the infusion set tubing attached and ready for insertion into a pump. The cartridge 1166 may be easily inserted into a peristaltic pump by placing the loop 1206 formed in tubing 1182 over the pump rotor and then placing the cartridge in a corresponding receiving structure in the pump. The cartridge 1166 and infusion set may easily be loaded into the pump. Additionally, the cartridge 1166 provides a larger structure to which the occluder 1162 is attached, providing a more secure manner of mounting the occluder 1162 in the pump and inhibiting movement of the occluder 1162.

The cartridge 1166 may also facilitate the creation of a flow channel around the occluder 1162. In a manner similar to that shown in FIG. 21, a projection may be used to create a flow channel around the occluder stop 994. The arm 1194 of cartridge 1166 shown in FIG. 24 may be used to support tubing 1182 at 1198 so as to facilitate the formation of such a flow channel by pressing against the tubing 1182 with a projection at area 1210. Thus, the cartridge 1166 may be used with a peristaltic pump having a corresponding recess for receiving the cartridge 1166 and a door for closing over at least a part of the cartridge 1166 and securing the cartridge into the pump, and a projection on the door. This allows a person to prevent free flow through the infusion line with the occluder prior to loading the infusion line into the pump, and to create a flow channel around the occluder after properly loading the infusion set and cartridge into the pump and closing the pump door. At such a point, the pump rotor prevents free flow through a properly loaded infusion set, as the tubing adjacent the rollers on a pump rotor is pinched closed.

Figure 25:
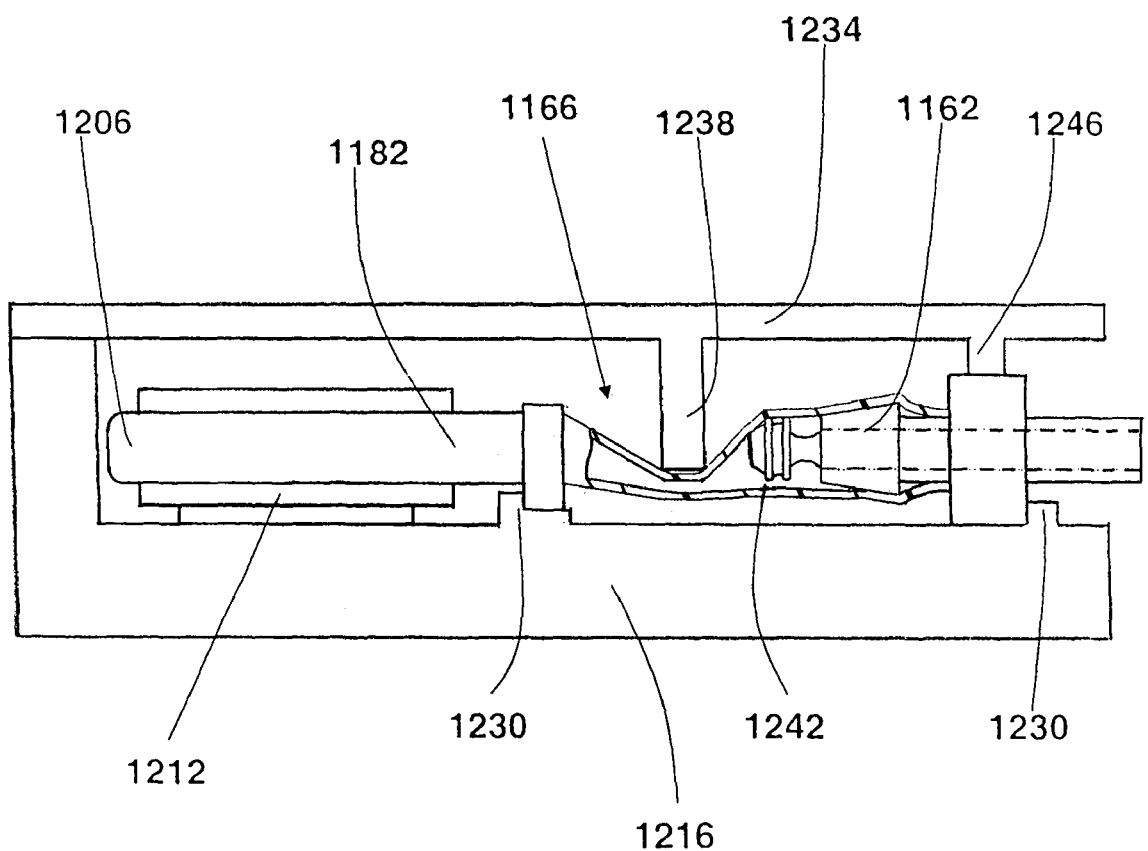
FIG. 25 shows a partially cut-away side view of a pump cartridge loaded into a pump according to the present invention.

Turning now to FIG. 25 a side view of a pump cartridge and infusion pump is shown. The pump cartridge 1166 is similar to that of FIG. 24 and includes the structures thereof, and has been loaded by placing the loop 1206 of tubing 1182 around pump rotor 1212. The pump 1216 is typically formed with projections 1230 to secure the cartridge 1166. A pump door 1234 is formed with a projection 1238 which forms a flow channel 1242 adjacent occluder 1162 as is discussed in relation to FIG. 21. The door 1234 may also be formed with one or more projections 1246 which contact the cartridge 1166 and hold the cartridge securely in the pump 1216.

The infusion set is thereby loaded into the pump 1216 in a manner which opens a flow channel 1242 around the occluder 1162 after proper loading of the infusion set. Free flow is prevented before and after loading by the occluder 1162 and rotor 1212 respectively. Opening a flow channel 1242 is advantageous as it reduces the pressure drop in the feeding or infusion solution caused by the occluder, and inhibits the blocking of the infusion set adjacent the occluder caused by particles in the infusion solution.

Thus, there is disclosed an improved apparatus and method for preventing free flow in an infusion line. The apparatus and method can be used with infusion control pumps, such as enteral feeding pumps or IV pumps, or as a replacement for such pumps. While the present disclosure discloses embodiments which are currently preferred, those skilled in the art will appreciate numerous modifications which can be made without departing from the scope and spirit of the present invention. For example, the relative size of the infusion set and occluder could be changed by providing an occluder which shrinks sufficiently under pressure to create fluid flow passages. The appended claims are intended to cover such modifications.

What is claimed is:

1. An occluder for use in an infusion set, the occluder comprising:
    a body having a proximal section and a proximal end, the proximal section and proximal end of the body being configured for disposition in the lumen of a piece of tubing of an infusion set;
    an arm attached to the proximal end of the body, the arm being smaller in diameter than the lumen of the piece of tubing so as to not contact the lumen;
    a stop attached to the arm and configured for disposition in the lumen of a piece of tubing of an infusion set, the stop having at least one generally annular rib formed thereon and configured for engaging the tubing to form a seal, and wherein the occluder is configured to selectively allow flow by allowing flow between the at least one generally annular rib and the tubing; and
    wherein the proximal endmost portion of the body contacting the lumen of the tubing where the body joins the arm is greater in diameter than the at least one generally annular rib.

2. The occluder of claim 1, wherein the proximal end of the body adjacent the stop is greater in diameter than the generally annular rib by between 0.01 and 0.06 inches.

3. The occluder of claim 1, wherein the at least one generally annular rib has a generally cylindrical outer surface having a bevel formed on each side thereof.

4. The occluder of claim 1, wherein the at least one generally annular rib has a generally cylindrical outer surface having a radius formed on each side thereof.

5. The occluder of claim 1, wherein the proximal portion of the stop is tapered and wherein the proximal end of the stop defines a generally flat surface generally perpendicular to the axis of the occluder.

6. An infusion set comprising the occluder of claim 1, and further comprising a section of tubing into which the body and the stop of the occluder are inserted.

7. The infusion set of claim 6, wherein the axis of the tubing adjacent to the occluder stop is disposed at an angle between about 10 degrees and about 40 degrees relative to the long axis of the occluder.

8. An infusion delivery system comprising the infusion set of claim 7, and further comprising a pump rotor, and wherein the axis of the tubing is disposed at an angle relative to the axis of the occluder by selectively positioning the occluder relative to the rotor.

9. An infusion delivery system comprising the infusion set of claim 7, and further comprising a projection, and wherein the projection presses on the tubing adjacent the occluder stop.

10. The infusion set of claim 7, wherein a flow channel is opened adjacent the stop due to the disposition of the tubing.

11. The infusion set of claim 7, wherein the angle is about 25 degrees.

12. A system comprising the occluder of claim 1, and further comprising an infusion tubing into which the body and stop of the occluder are disposed and an infusion pump, the infusion pump comprising a pumping mechanism and a bracket, wherein the bracket is configured for receiving the occluder and disposed such that the axis of the occluder is disposed at an angle relative to the bore of the tubing when the tubing and occluder are mounted into the pump.

13. The system according to claim 12, wherein the occluder is disposed at about a 25 degree angle relative to the tubing bore.

14. A system comprising the occluder of claim 1, and further comprising an infusion tubing into which the occluder body and stop are disposed, and an infusion pump, the pump having a projection disposed such that the projection presses on the tubing adjacent the stop so as to hold the tubing adjacent the stop at an angle relative to the occluder when the occluder and infusion tubing are mounted in the pump to thereby reduce the pressure necessary for fluid to flow past the occluder.

15. The system of claim 14, wherein the angle is between about 10 and 40 degrees.

16. The system of claim 14, wherein a flow channel is opened adjacent the stop between the stop and the tubing.

17. The system of claim 14, wherein the projection is formed as part of a pump door, and wherein the projection pushes against the tubing when the door is closed.

18. A method for selectively preventing flow in an infusion set comprising:
    selecting an occluder, the occluder comprising a body having a proximal end and a distal end and a stop attached to the proximal end of the body by an arm, the arm being smaller in diameter than the body; and
    disposing the occluder body and stop inside the bore of an infusion set tubing such that a seal is formed between the stop and the tubing, such that the proximal end of the body engages the tubing, and such that the arm does not engage the tubing; and
    wherein the end of the body nearest the occluder at the location where the arm attaches to the body contacts the bore of the tubing and is larger in diameter than the stop.

19. The method of claim 18 wherein the method further comprises selecting an occluder having a pair of generally annular ribs formed on the stop, and wherein the proximal end of the body is larger in diameter than the generally annular ribs.

20. The method of claim 18, wherein the method further comprises disposing a section of tubing adjacent the stop at an angle relative to the occluder sufficient to open a flow channel adjacent the stop.

21. The method of claim 18, wherein the method further comprises displacing a section of tubing adjacent the stop with at least one projection to thereby maintain the section of tubing adjacent the stop at an angle relative to the occluder.

22. The method of claim 21, wherein the method comprises engaging the projection to the tube by movement of a pump door.

23. The method of claim 18, wherein the method further comprises mounting the occluder into an infusion pump and closing a door of the infusion pump having at least one projection formed thereon such that the projection on the door displaces the tubing adjacent the stop.

24. The method of claim 18, wherein the method further comprises disposing the occluder and at least a portion of the infusion set in a pump having a pump rotor and disposing the occluder in the pump such that the occluder and pump rotor are oriented to position a section of tubing between the occluder and pump rotor at an angle relative to the occluder.

25. The method of claim 24, wherein the angle between the section of tubing and the occluder changes as the rotor rotates.

26. The method of claim 24, wherein the method further comprises positioning the section of tubing at an angle of about 25 degrees relative to the occluder.

27. The method of claim 18, wherein the method further comprises selecting an occluder wherein the stop has a rib formed thereon and wherein the proximal end of the body is greater in diameter than the rib.

28. A method for controlling flow in an infusion set comprising:
    selecting an infusion set, the infusion set having tubing with a bore therethrough;
    selecting an occluder having a body having a proximal end configured for disposition in the bore of the infusion set, the occluder having a stop attached to the proximal end of the body by an arm having a diameter less than an outer diameter than the stop, the stop being sufficiently large in diameter so as to form a seal between the stop and the tubing and thereby prevent flow past the stop;
    disposing the proximal end of the body and the stop of the occluder in the infusion set so as to prevent flow through the infusion set, and wherein, at the endmost portion of the body where the body is attached to the arm, the arm does not contact the tubing and the endmost portion of the body connected to the arm contacts the infusion set tube and is larger in diameter than the stop;
    disposing the infusion set in an infusion pump such that the pumping mechanism occludes flow through the tubing and such that a flow channel is created adjacent the stop so as to allow flow past the occluder.

29. The method of claim 28, wherein the method comprises positioning the tubing adjacent the occluder at an angle relative to the axis of the occluder so as to open a flow channel between the stop and the tubing.

30. The method of claim 28, wherein the method further comprises applying pressure to the tubing adjacent the stop so as to open a flow channel between the stop and the tubing.

31. The method of claim 28, wherein the method further comprises displacing the tubing adjacent the stop with a projection so as to open a flow channel between the stop and the tubing.

32. The method of claim 31, wherein the projection is part of the pump door.

33. The method of claim 28, wherein the method further comprises mounting the occluder in the pump such that the section of tubing between the pumping mechanism and the occluder is positioned at an angle relative to the axis of the occluder so as to open a flow channel between the stop and the occluder.

34. A method for selectively controlling free flow in a delivery set, the method comprising:
    selecting an infusion set having tubing having a bore and having an occluder disposed in the bore of the tubing to prevent flow of solution past the occluder, the occluder having a body with an end and a stop attached to the end of the body, wherein fluid flows through the body and exits the body to flow past the stop, and wherein the end of the body attached to the stop, at the location where the fluid exits the body, contacts the bore of the tubing and is larger in diameter than the stop;
    mounting the infusion set into an infusion pump so as to allow flow past the occluder.

35. The method according to claim 34, wherein the method comprises applying pressure to the tubing to open a flow channel past the occluder.

36. The method according to claim 34, wherein the method comprises applying force to the tubing adjacent the occluder.

37. The method according to claim 34, wherein the method further comprises applying force to the infusion set tubing to bend the tubing relative to the occluder.

38. The method according to claim 34, wherein the method comprises positioning the tubing adjacent the occluder at an angle of about 10 to 40 degrees relative to the occluder.

39. The method according to claim 34, wherein the method comprises positioning the tubing adjacent the occluder at an angle of about 25 degrees relative to the occluder.

40. An occluder for use in an infusion set, the occluder comprising:
    a body configured for disposition in a lumen of a piece of tubing of an infusion set;
    an arm attached to a proximal end of the body, the arm being smaller in diameter than the lumen of the piece of tubing so as to not contact the lumen;
    a stop attached to the arm and configured for disposition in the lumen of the piece of tubing of an infusion set, being configured for engaging the tubing to form a seal, and wherein the occluder is configured to selectively allow flow by allowing flow between the stop and the tubing; and
    wherein, at the location where the body attaches to the arm, the arm does not contact the tubing and the end of the body contacts the lumen of the tubing and is greater in diameter than the stop.

41. The occluder of claim 40, wherein the stop has an annular rib formed thereon, and wherein said end of the body is greater in diameter than the annular rib.

42. An infusion set comprising the occluder of claim 40, and further comprising a section of tubing into which the body and the stop of the occluder are inserted.

43. The infusion set of claim 42, wherein the axis of the tubing adjacent to the occluder stop is disposed at an angle between about 10 degrees and about 40 degrees relative to the long axis of the occluder.

44. The infusion set of claim 43, wherein a flow channel is opened adjacent the stop due to the disposition of the tubing.

* * * * *